(12) United States Patent
Loske et al.

(10) Patent No.: US 9,381,329 B2
(45) Date of Patent: Jul. 5, 2016

(54) VACUUM SPONGE DRAINAGE

(75) Inventors: Gunnar Loske, Ahrensburg (DE);
Tobias Paul Heinrich Schorsch,
Hamburg (DE)

(73) Assignee: LOHMANN & RAUSCHER GMBH & CO. KG, Neuwied (DE)

( * ) Notice: Subject to any disclaimer, the term of this patent is extended or adjusted under 35 U.S.C. 154(b) by 0 days.

(21) Appl. No.: 13/499,438

(22) PCT Filed: Jul. 22, 2010

(86) PCT No.: PCT/EP2010/060671
§ 371 (c)(1),
(2), (4) Date: Oct. 3, 2012

(87) PCT Pub. No.: WO2011/038949
PCT Pub. Date: Apr. 7, 2011

(65) Prior Publication Data
US 2013/0023840 A1     Jan. 24, 2013

(30) Foreign Application Priority Data

| Sep. 30, 2009 | (DE) | .......................... | 10 2009 043 472 |
| Dec. 9, 2009 | (DE) | .......................... | 10 2009 057 374 |
| Mar. 29, 2010 | (DE) | .......................... | 10 2010 013 271 |
| Mar. 30, 2010 | (DE) | .......................... | 10 2010 013 439 |
| Apr. 1, 2010 | (DE) | .......................... | 10 2010 013 848 |
| Apr. 1, 2010 | (DE) | .......................... | 10 2010 013 849 |

(51) Int. Cl.
*A61M 27/00*     (2006.01)
*A61M 1/00*     (2006.01)

(52) U.S. Cl.
CPC ............. *A61M 27/00* (2013.01); *A61M 1/0084* (2013.01); *A61M 1/0088* (2013.01); *Y10T 29/49826* (2015.01)

(58) Field of Classification Search
CPC ... A61M 27/00; A61M 27/002; A61M 1/008; A61M 1/0084; A61M 1/0088; A61M 1/0023; A61M 25/0021; A61F 13/00068
USPC ...................... 604/317–327, 540–544; 29/428
See application file for complete search history.

(56) References Cited

U.S. PATENT DOCUMENTS 3,394,702 A * 7/1968 Heimlich et al. ................. 604/1
5,891,111 A * 4/1999 Ismael .............. A61M 25/0021
138/116

(Continued)

FOREIGN PATENT DOCUMENTS

| DE | 10 2008 061535 | 6/2010 |
| WO | WO 03/028786 | 4/2003 |
| WO | WO 2004/041346 | 5/2004 |

*Primary Examiner* — Tatyana Zalukaeva
*Assistant Examiner* — Benjamin Klein
(74) *Attorney, Agent, or Firm* — Stinson Leonard Street LLP

(57) ABSTRACT

The invention relates to a vacuum sponge unit (2) for use in human or animal bodies, comprising a fluid collecting member (10), in particular a sponge unit, and a fluid communication member (20), in particular a drainage tube, which is disposed at least partially in the fluid collecting member (10) and is connected in fluidic communication to the fluid collecting member (10). In order to improve known devices, the inventions proposes developing the vacuum sponge unit (2) such that the fluid collecting member (10) has a channel (11) for guiding a guide member (3), in particular a guide wire, and/or a delivery member (4), in particular a probe unit and/or an endoscope, through the fluid collecting member (10).

6 Claims, 35 Drawing Sheets

(56) References Cited

U.S. PATENT DOCUMENTS

| | | | | |
|---|---|---|---|---|
| 6,123,697 | A * | 9/2000 | Shippert | A61B 17/12022 604/104 |
| 8,398,613 | B1 * | 3/2013 | Hahn | A61M 27/00 604/101.01 |
| 2003/0109855 | A1 * | 6/2003 | Solem et al. | 604/540 |
| 2006/0116691 | A1 * | 6/2006 | Bonacci | 606/108 |
| 2007/0219497 | A1 * | 9/2007 | Johnson | A61M 27/00 604/131 |
| 2007/0282310 | A1 | 12/2007 | Bengtson et al. | |
| 2009/0005750 | A1 * | 1/2009 | West | 604/385.03 |
| 2011/0319804 | A1 * | 12/2011 | Greener | A61F 13/00987 602/46 |
| 2012/0296207 | A1 * | 11/2012 | Chernomorsky et al. | 600/431 |

* cited by examiner

VACUUM SPONGE DRAINAGE

CROSS REFERENCE TO RELATED APPLICATIONS

This application is the U.S. National Stage of International Application Number PCT/EP2010/060671 filed on Jul. 22, 2010 which was published on Apr. 7, 2011 under International Publication Number WO 2011/038949, and which claims priority to German patent application 102009043472.0 filed on Sep. 30, 2009, German patent application 102009057374.7 filed on Dec. 9, 2009, German patent application 102010013271.3 filed on Mar. 29, 2010, German patent application 102010013439.2 filed on Mar. 30, 2010, Germany patent application 102010013849.5 filed on Apr. 1, 2010 and German patent application 102010013848.7 filed on Apr. 1, 2010.

TECHNICAL FIELD

The invention relates to a vacuum sponge unit for use in human or animal bodies, comprising a fluid collecting member, in particular a sponge unit, and a fluid communication member, in particular a drainage tube, which is disposed at least partially in the fluid collecting member and is connected in fluidic communication to the fluid collecting member. The invention further relates to a vacuum sponge system comprising a vacuum sponge unit and a guide member and/or delivery member, a method for inserting the vacuum sponge system into a human or animal body, a method for manufacturing a vacuum sponge unit, use of a fluid-collecting material to manufacture a vacuum sponge unit, use of a vacuum sponge system in a human or animal body and use of a vacuum sponge unit as a suction attachment.

BACKGROUND OF THE INVENTION

WO 2004/041346 A1 describes an endoscopic wound care treatment system. WO 2004/041346 A1 relates _ more specifically to an endoscopic component which also permits the application of intracorporeal negative pressure therapy in a human or animal body.

SUMMARY OF THE INVENTION

The object of the present invention is to provide a development of WO 2004/041346 A1 which eliminates or at least reduces the disadvantages of the prior art system.

This object is achieved according to the invention by the fluid collecting member having a channel for guiding a guide member, in particular a guide wire, and/or a delivery member, in particular a probe unit and/or an endoscope, through the fluid collecting member.

The invention is based on the realization that use of the device in WO 2004/041346 A1 in intracorporeal regions of the human or animal body deeper than approximately 10 cm in the human or animal body (as seen from the body orifice) leads to application problems. The inventor has also realized that the field of application of the device in WO 2004/041346 A1 is limited in particular to intracorporeal regions that are open on one side only and that it is problematic to use it in channel-like intracorporeal regions which are open on two sides.

The inventor, Dr Gunnar Loske, has invented a development of the device in WO 2004/041346 A1 in the course of his work at the "Marienkrankenhaus" hospital in Hamburg, Germany. The development advantageously makes the vacuum sponge unit according to the invention suitable for intracorporeal regions of the human or animal body that are located deeper than 10 cm (as seen from the body orifice) inside the human or animal body, and allows the vacuum sponge unit to be used not only in intracorporeal regions that are open on one side, but particularly advantageously in channel-like intracorporeal cavities that are open on two sides (in particular in the entire gastrointestinal tract).

The invention is based on the idea that these and other advantages can be achieved by disposing a channel inside the fluid collecting member, said member being more specifically a sponge unit.

The channel can be used to guide a guide member, in particular a guide wire (or also a probe, sleeve, rod or endoscope), through the channel in order to guide and position the fluid collecting member along the guide member. In WO 2004/041346 A1, positioning is achieved by the fluid collection means unfolding itself at the outlet of the inner sleeve, which has the disadvantage that wound care can only be applied to intracorporeal regions which can be reached with the inner sleeve. The invention removes this disadvantage by allowing the fluid collecting member to be positioned in remoter and winding regions of the body by means of a guide member which is guided inside the channel.

The channel can be used additionally or alternatively to insert a delivery member into the body. A disadvantage of the device in WO 2004/041346 A1 is that, if it were used in the entire gastrointestinal tract, feeding or intestinal evacuation would only be possible after removing the fluid collection means. This disadvantage is eliminated, according to the invention, by the channel being adapted to accommodate a delivery member, for example for feeding, intestinal evacuation, degassing and/or for flushing parts of the intestine located orally or aborally in relation to the sponge, such that the fluid collecting member does not need to be removed during such processes.

The channel can be used additionally or alternatively to dispose a delivery member intracorporeally. In WO 2004/041346 A1, the endoscope is firstly removed from the body before the fluid collection means is subsequently inserted. This means that, once the fluid collection means has been positioned and activated, visual monitoring by means of the endoscope is no longer possible, or is a complex and laborious process. The invention removes this disadvantage by making the channel provide space for an endoscope, for example, thus permitting simultaneous use of a fluid collecting member and an endoscope. It is also possible, during or after activation of the fluid collecting member, to provide or insert an endoscope, for example, in order to monitor the condition of the intracorporeal region being treated and to check the placement of the fluid collecting member.

It is particularly preferred when the fluid collecting member is a sponge unit. The sponge unit performs the function of conducting fluids and gases into or out of the body. This is the function of pressure distribution, more specifically, so that a negative pressure applied to the fluid communication member causes the sponge unit and the intracorporeal region surrounding it to collapse.

The invention preferably relates to an insertion system for positioning a sponge drainage unit in an intestinal lumen, a hollow organ, a body cavity or a tissue abscess, wherein said system comprises a guide wire, a polyurethane sponge which is connected to a drainage tube and which is located with a positioning sleeve inside a guide sleeve, wherein said polyurethane sponge has an X-ray marker. The insertion system is preferably adapted for sponge drainage in endocavitary (or intracavitary) or endoluminal (or intraluminal) vacuum sponge therapy.

It is known that, by inserting a drainage unit connected to an open-pored polyurethane sponge, it is possible to treat internal wounds in cases of postoperative rectal anastomotic insufficiency. The drainage unit is placed under suction, removes wound exudates and results in wound closure and healing. Only wounds near body orifices can be treated with the insertion system available hitherto.

Advantages which can be achieved with the present invention consist in deeper positioning of a sponge drainage unit and the broader resultant scope for vacuum sponge therapy. By means of the invention, the sponge system can also be placed in the esophagus, the stomach, the duodenum, the large intestine and in any body cavities or wound cavities that can be reached with an endoscope. By positioning the sponge system in an intestinal lumen, it is possible to achieve complete closure of same. Internal wounds can also be drained and closed simultaneously and made to heal as a result. An esophageal perforation can be treated endoscopically by means of a covered, self-expanding stent. The latter is inserted above the defect by an insertion system via guide wires previously inserted endoscopically and is designed to seal the defect from the inside. This also requires an externally inserted wound drainage unit. By means of the invention, the insertion system is positioned via an endoscopically inserted guide wire, and an open-pored polyurethane sponge connected to a drainage unit is inserted above the perforation defect in the esophagus. The drainage unit is placed under negative pressure by means of a vacuum pump. This causes the esophageal lumen above the sponge to collapse, the defect to close and wound exudate to be drained simultaneously. The advantage of this method compared to the stent system is that the wound exudate is drained inwardly and removed via the drainage unit due to the suction effect in the direction of the intestinal lumen. This is efficacious, in particular, when applied to organs that are naturally under negative pressure (organs in the thoracic cavity) or to wounds and wound cavities that are in contact with the thoracic cavity and which are physiologically under negative pressure as a consequence. Due to the vacuum suction applied via the drainage unit at the open-pored polyurethane sponge, the wound exudate can be removed via the drainage unit and is not drawn in the direction of the thoracic cavity along the physiological pressure gradient and during respiratory movements.

The invention preferably relates to a slit overtube (protective sleeve) for inserting and changing endoscopes and delivery members into an intestinal lumen, a hollow organ, a body cavity or tissue abscess via natural or also via artificial body orifices.

Protective sleeves, so-called overtubes, are used in endoscopic examinations of the gastrointestinal tract, in particular of the esophagus and the stomach, but also of the small intestine. They are pushed over the endoscope prior to the examination and are advanced over the placed endoscope into the intestine after insertion of the endoscope into the intestinal lumen. Once in place, overtubes are used for safely bypassing the pharyngeal cavity and the esophagus when performing endoscopic treatment of various kinds. Particularly when insertion of an endoscope into the pharyngeal cavity and the upper esophagus is difficult, and an endoscope must be inserted and removed repeatedly during the examination, it is possible to prevent injury to the pharynx and the esophagus wall because the overtube serves as a protective sleeve and splint for the endoscope. Overtubes are used to prevent injuries to the intestinal wall during endoscopic removal of foreign bodies. During endoscopic examination of the small intestine, overtubes are used as splint and protection when bypassing the esophagus, the stomach or the small intestine, and as a technical aid for reaching deeper sections of the intestine. Overtubes available hitherto are pushed onto the endoscope before an endoscopic examination, after which the endoscope is inserted via a body orifice, the overtube advanced further up the endoscope and placed as a splint. The endoscopic examination is then performed via the placed overtube. Flexible endoscopic operations are currently performed using special instruments that are inserted via working channels of the flexible endoscope. In the case of endoscopic operations with rigid endoscopes, e.g. abdominoscopies, a rigid optical instrument is inserted via a trocar into a body cavity and other, additional rigid instruments are deployed via trocars inserted through separate incisions. More recently, operation instruments have been deployed along with the optical instruments via a single port.

According to the invention, the overtube is designed such that it is slit longitudinally along its entire length. The invention can be adapted with regard to diameter and length to the respective conditions. It basically consists of a pliable yet shape-retaining plastic tube. The advantages to be achieved with the invention involve the possibility of attaching and removing an overtube to or from an endoscope at any time during an endoscopic examination. The overtube can be placed around the endoscope via the longitudinal slit, thus resulting in the endoscope coming to rest inside the overtube. The overtube with the endoscope can then be inserted as a splint into a body orifice. It is possible to remove the overtube, while the endoscope is still inserted, by pulling it out laterally via the slit. By virtue of the invention, numerous novel ways and means of providing endoscopic treatment are made possible. The invention allows a plurality of medical instruments to be inserted into the body in a technically simple and safe manner via a body orifice. It is possible, for example, to insert both a gastroscope and a medical instrument into the stomach. To do so, the overtube is firstly placed over the gastroscope that is already in the stomach and is then inserted into the stomach. The gastroscope is then removed so that another piece of medical apparatus (e.g. a drainage unit or a pair of semiflexible endoscopy forceps) can then be inserted under endoscopic view along with the gastroscope via the overtube into the stomach. The overtube can then be retracted and removed, while leaving the instruments in place in the stomach. It then can only be placed back over the endoscope and pushed forwards again as far as the stomach. This placement maneuver can be repeated several times, which means it is possible in this way to place a plurality of instruments simultaneously into the stomach using a gastroscope. By virtue of the invention, it is possible to operate with semiflexible instruments with flexible endoscopic visual control. The semiflexible instruments can be introduced into the stomach as described in the foregoing. The endoscope is used as an optical system for operating the semiflexible instruments and for delivering the test gas. In order to perform an endoscopic operation, the overtube can be removed to prevent loss of gas and to minimize the frictional resistance. The invention allows the same operative techniques to be used as are known from rigid endoscopy, such as abdominoscopy. It will also be possible to perform natural orifice transluminal endoscopic surgery (NOTES) procedures. For example, the stomach wall can be opened under flexible endoscopic visual control in order to open the abdominal cavity and to perform special operative procedures using the semiflexible instruments that are inserted. The overtube is preferably inserted over a previously inserted probe, guide wire or instrument.

The overtube may also be used to remove polyps or to perform endoscopic operations. For example, after polypectomy the overtube may be placed laterally over the endoscope and advanced under endoscopic view as far as the removal point. The polyp can then be pulled out using the endoscope, and the overtube remains in place inside the intestine. After extracting the polyp, the endoscope can be inserted again via the overtube that is in place. Using the overtube reduces the time needed for examination and improves patient safety, because when the overtube is in place, the intestine does not have to be endoscoped again when reinserting the endoscope. Instead, the overtube can be used as a guiding splint to access the site to be examined.

The invention preferably relates to a sponge suction attachment for extracting body fluids, wound exudates, flushing solutions or gases, comprising a drainage tube which is connected to a fluid collection means. The fluid collection means preferably has an X-ray marker. It is preferable that the fluid collection means includes an elastically compressible structure with fluid channels. The fluid collection means preferably includes an open-pored polyurethane sponge. The drainage tube preferably has lateral openings at its distal end. The drainage tube is preferably of plastic, or preferably of metal. Another drainage tube flush with the first drainage tube can preferably be inserted in a final step into the latter, like into a sleeve, such that extraction by suction is performed with the second drainage tube. The invention also relates to a fluid collection means having an opening into which the distal end of a drainage tube can be inserted, with the result that a conventional suction attachment can be used as a sponge suction attachment. The fluid collection means preferably has a means of attachment (sticky tape, thread, Velcro tape) for attaching it to the distal end of a drainage tube.

During operations, wound exudate and flushing solution are usually removed with a suction attachment which is connected to a suction tube. Conventional suction attachments comprise a tube, at the distal end of which there are one or more perforation openings. Conventional suction attachments often adhere to soft tissue, and clogging of the perforation openings is also a frequent occurrence.

The invention can be applied in all operations, including minimal invasive surgery, laparoscopies, thoracoscopies and conventional abdominal surgery. The invention can also be applied in non-medical fields if the aim is to remove liquids. According to the invention, an open-pored polyurethane sponge is secured over the perforation openings to the distal end of a drainage tube functioning as a suction attachment. This sponge acts like a filter and simultaneously prevents the suction attachment from adhering to soft tissue. Infectious plaque on soft tissue or organs can be wiped off with the sponge. In this way, it is possible to clean soft tissue or organs efficiently and gently. The invention can be put to good use to perform operations in cases where the site of the operation is infected (e.g. peritonitis). In narrow cavities and when there is direct contact with tissue, it is possible to draw off exudate through the open-pored sponge. Until now, this has been difficult to achieve with a conventional suction device. The invention can be produced in various different forms:

Variant 1: An open-pored sponge is secured via the perforation openings at the distal end of a suction attachment by adhesion, suture or other forms of attachment. To achieve this, the sponge is slit down the middle or has a central punch-out into which the distal end of the suction attachment can be inserted. It is possible to convert an existing suction attachment to one according to the invention by placing and securing a sponge.

Variant 2: An open-pored sponge is secured over the distal end of a suction sleeve that has perforation openings at its distal end. A suction attachment can be inserted into such a sleeve. The sleeve is flush with the suction attachment at the proximal end so that a vacuum can be generated at the sponge when suction is performed. In an operation, this variant has the advantage that, owing to the possibility of pulling off the sleeve, one can not only exploit the advantages of extracting through a sponge sheath, but can also use conventional, direct extraction with the suction attachment alternately.

The invention preferably relates to a sponge drainage system for endoscopic, radiological or operative insertion into an intestinal lumen, a hollow organ, a body cavity or a tissue abscess, the sponge drainage system comprising a guide member and the drainage system (a fluid collection means connected to a drainage line). The invention also relates to a drainage system in which the fluid collection means has an X-ray marker. It is preferable that the fluid collection means includes an elastically compressible structure with fluid channels. The fluid collection means preferably includes an open-pored polyurethane sponge. The guide member is preferably a wire. The guide member is preferably made of plastic. The tip of the guide member is preferably soft and flexible. The drainage line is preferably a tube. The drainage line preferably has drainage openings at its distal end. It is preferred that the drainage line has lateral openings at its distal end that extend over the entire length or incomplete length of the fluid collection means. An additional drainage line is preferably inserted into the sponge. The additional drainage line can preferably be moved inside the fluid collection member. The additional drainage line is preferably attached securely inside the fluid collection member. The distal tip of the additional drainage line is preferably rounded. It is preferable that the additional drainage line likewise includes a guide member. The fluid collection means preferably tapers conically at its distal end. The fluid collection means preferably tapers conically at its proximal end. It is preferred that a plurality of fluid collection means are attached to a drainage tube. The sponge drainage system is preferably adapted for intraluminal and intracavitary vacuum sponge therapy in the entire gastrointestinal tract, for draining body cavities, hollow organs, tissue abscesses, intestinal lumina, for placement via natural or artificial body orifices with the simultaneous possibility of additional decompression, flushing or feeding remotely from the sponge when the sponge is intraluminally positioned.

It is known that, by inserting a drainage means connected to a polyurethane sponge, it is possible to treat internal wounds in cases of postoperative rectal anastomotic insufficiency. A constant suction force is applied to the drainage means in such cases. Exudation can be conducted inwards, the wounds clean themselves and heal.

Esophageal defects caused by perforations or postoperative anastomotic insufficiency can be treated by intraluminal insertion of a polyurethane sponge. This is done by inserting a sponge drainage means into the intestinal lumen over the defect. When the drainage means is then placed under suction, the intestinal lumen closes and the defect can bond and heal. The efficacy of the intraluminal therapy could also be demonstrated on the duodenum. Vacuum sponge therapy allows these injuries to be treated endoscopically. Only rectal anastomotic insufficiencies near body orifices can be treated with the insertion system available hitherto.

The invention provides numerous advantages and novel options for treatment. The invention relates to a sponge drainage unit that is placed in an intestinal lumen, for example, under endoscopic, radiological or operative view. The drainage means is put in place by advancing it over a previously inserted guide wire. A guide wire is inserted intraluminally by endoscopy, and the sponge drainage unit is subsequently advanced along the guide wire with precision to the desired placement site under endoscopic, radiological or operative control. The invention can be inserted intraluminally to any position in the entire gastrointestinal tract. Novel options for treatment are provided by inserting an additional drainage tube into the sponge. If this additional drainage tube is designed to be displaceable within the sponge, it can be advanced or even removed after the sponge drainage unit has been positioned. If, for example, an esophageal injury is being treated, the additional drainage tube can be advanced into the stomach and enteral nutrition or decompression performed in order to relieve the stomach. These techniques are also possible when the sponge is placed under negative pressure and the esophageal lumen closes. Due to the negative pressure, the sponge attaches itself by suction to the intestinal lumen in such a way that the sponge cannot be displaced, and it also makes the additional drainage tube adhere, thus fixing the latter inside the passage through the sponge. When treatment is performed anally and the large intestine is closed, for example to ensure anastomosis or to temporarily bypass a section of intestine with the invention, it is possible for intestinal gases or stool to exit via this additional tube (located at the oral end of the temporary intestinal closure achieved endoscopically) and for the large intestine to be decompressed. Endoscopic flushing is also possible. Intraoperative intraluminal placement in the small intestine is also possible. The sponge can be used, for example, to treat a perforation of the small intestine by inserting it as far as a perforation or an anastomosis. The intestinal lumen is temporarily closed by the vacuum, thus allowing a defect to heal. Enteral nutrition can be carried out simultaneously by means of an additional probe, the distal end of which comes to rest aborally from the sponge.

The invention relates preferably to a drainage system for extracting body fluids, wound exudates, gases from body cavities, hollow organs, tissue abscesses, intestinal lumina, for provisional endoscopic closure of intestinal lumina, not only via natural but also via artificial body orifices, the drainage system comprising a drainage tube, fluid collection means and an overtube sleeve for an endoscope. The fluid collection means preferably has an X-ray marker. It is further preferred that the fluid collection means is of tubular design and has a central lumen. The fluid collection means preferably includes an elastic compressible structure with fluid channels. The fluid collection means preferably includes an open-pored polyurethane sponge. One or more drainage lines are preferably fixed inside the fluid collection means. The drainage lines are preferably tubes. The drainage line preferably has lateral drainage openings at its distal end. The drainage line is preferably provided at its distal end with lateral drainage openings over the entire length that is in the fluid collection means. The invention also relates to an overtube for an endoscope of the kind described above, wherein the overtube consists of a plastic tube.

In the prior art, open-pored polyurethane sponges are inserted into wounds, outwardly sealed with a film, connected to a drainage tube and placed under suction with the aid of a vacuum pump system, in order to treat secondarily healing wounds. The wound collapses under the negative pressure, and the wound exudate is continuously or intermittently sucked out from the wound. The wound can rapidly clean itself, reduce in size and form granulation tissue. It has been proven on wounds resulting from suture ruptures after rectal operations that this form of treatment can also be applied efficaciously to internal wounds. To do so, a polyurethane sponge is inserted through the suture rupture into a wound cavity behind the rupture.

It has likewise been shown that vacuum sponge therapy is also efficacious on deeper internal wounds that can only be reached with an endoscope, for example on wounds resulting from operations on, or injuries to the esophagus or the duodenum. Such treatment involves inserting a vacuum sponge drainage unit under endoscopic view either via a defect into a wound cavity, or the sponge drainage unit is inserted into the intestinal lumen via the defect. Complete provisional closure of the intestinal lumen has been achieved in this manner. This artificial intestinal closure by vacuum sponge drainage can be used as a means of treatment. Contamination of the internal wound by digestive secretions is prevented, the wound exudates are simultaneously sucked out, the wound can clean itself and defects can close simultaneously as a result of the suction effect created by the vacuum suction at the sponge. Endoscopic placement of a sponge drainage unit may involve technical difficulties. Only internal wounds close to the skin can be treated with currently available systems.

Endoscopic placement of a vacuum sponge drainage unit is made technically more simple by the invention. The new options for medical treatment that are generated by draining internal wounds or by inducing closure of the intestinal lumen are numerous and diverse.

The invention relates to an open-pored polyurethane sponge of tubular shape and variable length. This sponge is fixedly attached to the distal end of a drainage tube which has perforation openings at its distal end. The sponge is placed onto an endoscope which is guided through an overtube, and is displaceable on said endoscope. The overtube is a tube-like sleeve which can be moved over the endoscope. The overtube is proximal to the tube-shaped drainage sponge. It prevents the sponge on the endoscope from slipping in a proximal direction. The overtube is also used as pusher in order to guide the drainage sponge slidingly along the endoscope in the distal direction and to push it off the endoscope and thus release it. In this way, it is possible to insert a sponge drainage unit into a wound or body cavity or, for example, intraluminally into an intestinal lumen or hollow organ. A negative pressure is applied to the sponge drainage unit as soon as it is released, thus causing it to adhere. The endoscope can then be removed.

Prior to placement of the sponge, it is possible in the same step to advance a probe via the working channel of an endoscope. When a sponge drainage unit is inserted endoscopically in the esophagus, enteral feeding or the oral administration of medicines is made possible via a probe inserted as far as the stomach or small intestine, for example.

The invention preferably relates to a drainage system for extracting body fluids, wound exudates and gases from body cavities, hollow organs, tissue abscesses, intestinal lumina, comprising drainage lines, fluid collection means and connector members for the drainage lines. The fluid collection means preferably includes an elastic compressible structure provided with fluid channels. The fluid collection means preferably includes an open-pored polyurethane sponge. One or more drainage lines are preferably fixed inside the fluid collection means. The drainage lines are preferably tubes. The drainage line preferably has lateral drainage openings at its distal end. The drainage line is preferably provided at its distal end with lateral drainage openings over the entire length that is in the fluid collection means. It is preferred that the fluid collection means can be divided into smaller drainage system units. The fluid collection means is preferably provided with perforation slits to enable it to be divided into smaller drainage units. It is preferred that the drainage tubes can be connected to each other by means of connector members.

After operations, drainage tubes are normally inserted to remove wound exudates, body fluids and pus. The purpose of these drainage tubes is to remove secretions via lateral openings along the drainage path, by gravity drainage and overflow drainage. Drainage members may be designed as drainage tubes or also as flat drainage tubes. In the latter case, drainage is also achieved by capillary action. Drainage tubes connected to a source of negative pressure are also inserted. However, wound drainage units mostly only take effect immediately after an operation, because drainage openings are quickly clogged due to fibrin deposition, coagulation of blood and adherence of tissue.

In recent years, vacuum sponge therapy has become established in the treatment of open wounds allowed to heal by secondary intention. A polyurethane sponge inserted into a wound and closed with a film dressing is used as a filter for continuous, long-term wound drainage over a period of days. The wounds clean themselves quickly in most cases, and even problematic wounds can be made to heal in this way. Endoscopic vacuum sponge therapy has also been applied successfully to treat internal wounds that arise as a result of anastomotic insufficiencies or intestinal perforations. In order to treat septic wounds in the abdominal cavity, for example in cases of peritonitis, polyurethane sponges are likewise used to remove secretions. These wound dressings, which are sometimes of large area, with a film in the form of an occlusive dressing on the open abdomen, are placed under negative pressure by means of one or two drainage attachments.

The invention provides several improved and extended options for applying vacuum sponge therapy. The invention relates to an open-pored sponge provided with drainage tubes and which can be subdivided into smaller subunits. The drainage tubes are connected to each other via a connector member. The invention permits vacuum sponge drainage units to be placed exactly at the actual intra-abdominal septic focus, for example in abdominal surgery. Drainage is also possible from the "lowest points" at which wound liquids or wound exudate can accumulate in the abdominal cavity. Placement in hollow organs, such as an intestinal lumen, is also possible. This provides new treatment options.

The invention can be inserted operatively into the abdominal cavity, in the form of sponge packets of large area, although it is also possible to subdivide the vacuum sponge unit into a plurality of subunits. To this end, the sponge is pre-perforated at subunit boundaries so that the subunits can be obtained by simply pulling the units apart from each other. The single drainage tubes are connected to each other inside or outside the abdominal cavity via connector members, such that only one single tube needs to be connected to a source of negative pressure. A negative pressure can thus be applied to all the subunits. It is possible to rinse the drainage tubes and to use them as rinsing tubes in order to perform "rinsing/suction treatment".

Due to the perforated end of the drainage tube being secured inside the sponge over the entire length of a sponge member, one advantage of the invention is that the sponge contracts in width when negative pressure is applied, but only insignificantly in length. The original placement of the sponge is thus secured.

The invention is to be used in those cases in which repeated, short-term surgery is to be expected due to septic conditions ("relaparotomies"). The inventive device must normally be inserted and removed under conventional operative conditions (i.e., body cavity opened by incision). Its application will initially be limited to severe septic syndromes, as there is a risk of organs being iatrogenically injured by direct suction at the sponge. After the abdomen has been opened, the vacuum sponge drainage unit is precisely placed and the abdominal cavity is subsequently closed with a suture so that suction can be re-established y the cavity being closed again. It is also possible for the invention to be used in combination with an air-tight film dressing to close the abdominal cavity. Placement of the inventive device is also possible with minimal invasive surgery, e.g. laparoscopically. The invention can also be used in other body cavities, in the thoracic cavity, in infected cavities, in organ cavities, in tissue abscesses, intestinal lumina, etc.

Embodiments containing combinations of the features described in the foregoing are particularly preferred.

The channel is preferably disposed parallel to a longitudinal axis of the fluid collecting member. It is preferred that the fluid collecting member is circular or cylindrical in shape, in particular, and that the channel is disposed parallel to the cylindrical fluid collecting member. The longitudinal axis of the fluid collection member is preferably the axis that is oriented substantially parallel, when the fluid collection member is used in the intended manner, to the inner wall of the body region in which the fluid collecting member is disposed. It is further preferred that the channel is disposed along an axis of symmetry of the fluid collecting member. The fluid collecting member is preferably tubular, the channel being the inner cavity in the tubular fluid collecting member. It is preferred that the channel has a first opening as an inlet for the guide member and/or the delivery member, and a second opening as an outlet for the guide member and/or the delivery member. It is preferred that the first opening and the second opening are disposed on substantially opposite surfaces of the fluid collecting member. What this advantageously achieves is that the channel for guiding the guide member, in particular a guide wire, and/or for guiding the delivery member, in particular a probe unit and/or an endoscope, is used by the fluid collecting member such that the channel forms a connection between the proximal and distal ends of the fluid collecting member. When the channel is disposed symmetrically in the fluid collecting member, this creates the advantages that the fluid collecting member collapses in a particularly uniform manner about a drainage tube disposed in the channel, for example, if the drainage tube applies a negative pressure, that medicines which are supplied to the fluid collecting member via a delivery member disposed in the channel are distributed particularly uniformly in the fluid collecting member and on the surface thereof, and that guidance along the guide member is particularly simple, since the fluid collecting member is disposed at an identical radius about the guide member. When the channel is disposed outside the axis of symmetry of the channel, but parallel to it, this provides the advantages that a specific region of the body, in which the fluid collecting member is disposed when used in the intended manner and which is closer to the channel than the opposite intracorporeal region, can be exposed to the influences of negative pressure, administration of medicines, etc. more intensively than the opposite region. Disposing the channel parallel, and particular in a straight line, provides the advantage that the frictional force that arises when guiding the fluid collecting member along the guide member and when inserting the delivery member into the fluid collecting member can be advantageously reduced. In this way, moving the fluid collecting member in relation to the guide member and/or the delivery member is advantageously simplified.

The fluid collecting member preferably has a longitudinal slit along the longitudinal axis of the fluid collecting member, said longitudinal slit extending between the surface of the fluid collecting member and the channel. The longitudinal slit preferably extends between the distal end and proximal ends and over the entire length of the fluid collecting member. The longitudinal slit is preferably designed in the same way as the longitudinal slit of the overtube. The longitudinal slit preferably extends in the radial direction of the fluid collecting member between the channel and the surface of the fluid collecting member which is closest to the channel. A fluid collecting member with a longitudinal slit provides the advantage that it can be placed onto an endoscope, a guide member, a delivery member, etc. at any time and inserted into the body, without having to remove the endoscope or the like. What can also be advantageously achieved is that a fluid collecting member which is already in use can be replaced with a fresh fluid collecting member, without the endoscope or the like having to be removed during the replacement process. Other advantages analogous to those described for the overtube with longitudinal slit can also be achieved. After lateral placement on the guide/delivery member, in particular the endoscope or probe, the longitudinal slit in the fluid collection means and/or the overtube is preferably closed, in particular by means of a suture, an adhesive bond, or the like. Various closure mechanisms for the fluid collection means and/or the overtube are preferred. The closure mechanisms are designed to close the longitudinal slit completely or only partially (for example at the tip only), in order to simplify guidance along the guide member, for example along an endoscope. It is preferred that closure is complete, for example by a kind of zip fastener. In this way, guidance can be achieved advantageously in regions remote from the body orifice and around kinks or corners.

The fluid collecting member preferably has an X-ray marker which is designed to be detected during roentgenography. The X-ray marker is preferably disposed on the surface of the fluid collecting member. The X-ray marker is preferably disposed as a circle around a rotationally symmetrical fluid collecting member. The X-ray marker is preferably disposed inside the fluid collecting member. Disposing an X-ray marker on the fluid collecting member has the advantage that it is possible to position and completely remove the fluid collecting member in a controlled manner and to monitor the fluid collecting member when the vacuum sponge unit is used in the intended manner.

The fluid communication member is preferably inserted into the fluid communication member through a fluid collecting member opening and extends along the entire length of the fluid collecting member. The fluid communication member preferably extends along the entire longitudinal axis and/or axis of symmetry. What this advantageously achieves is that the influence of the fluid communication member (applying a negative/over-pressure, introduction of a medicine, etc.) is substantially identical over the entire length of the fluid collecting member. What is also achieved is that the positioning of the fluid collecting member, in particular of the distal end of the fluid collecting member, remains substantially unchanged when the fluid communication member delivers a negative to pressure, an over-pressure, a medicine, etc. to the fluid collecting member.

The fluid communication member is preferably disposed in the channel. Alternatively, it is preferred that the fluid communication member is disposed outside the channel. The fluid communication member is preferably disposed in the fluid collecting member such that it is spaced apart from the guide member and/or the delivery member. It is preferred that the guide member and delivery member is disposed in the fluid communication member, in particular in the drainage tube. In one preferred embodiment, a feeding tube is disposed in the drainage tube and adapted to be advanced therein, which means that a feeding tube can be inserted through the channel, even after the fluid collecting member has been put in place, or can be placed in such a way from the outset, thus saving space in an advantageous manner. Depending on the type of body region to be supplied, a particularly compact design of the vacuum sponge unit can be achieved. Depending on the anatomy of the region being supplied, and on the intracorporeal path to that region, the fluid communication member can be disposed advantageously in relation to the guide member and/or the delivery member.

The fluid communication member is preferably adapted so that it can be connected in fluidic communication to a vacuum pump, in particular to an electric vacuum pump. The vacuum pump is preferably designed to apply a negative pressure and/or an over-pressure to the fluid communication member. The fluid communication member has an adapter for connecting it directly or indirectly to the vacuum pump. This advantageously allows a negative pressure to be applied particularly efficiently and precisely to the fluid collecting member. The negative pressure is continuous or intermittent. Since the sponge is fixed in position by suction when placed endoscopically, there is always a certain negative pressure, otherwise the sponge could be dislocated. It is also preferred that the negative pressure is applied intermittently and fluctuates between negative pressures (e.g. between 80 and 125 mm Hg). This has the advantage that the tissue pressure produced by the sponge can cause less potential pressure injury to the tissue than when fixation is achieved by the negative pressure.

The fluid communication member is preferably connected fixedly to the fluid collecting member. It is preferred that the fluid communication member is bonded, welded, sewn or otherwise mechanically fixed to the fluid collecting member. A particularly reliable fluidic communication is advantageously achieved in this manner between the fluid communication member and the fluid collecting member. Another advantage is that the fluid collecting member can be removed from the body on the fluid communication member.

The fluid communication member preferably has a plurality of openings in the particular region thereof which is disposed inside the fluid collecting member. The openings are preferably perforations. It is preferred that the openings are disposed symmetrically in the surface of the fluid communication member. The openings are preferably disposed only on one side of the fluid communication member surface, so that the fluid collecting member collapses asymmetrically around the fluid communication member. By means of the plurality of openings, the influence of the fluid communication member on the region of the fluid collecting member opposite the openings is distributed substantially uniformly.

The vacuum sponge unit preferably has an additional fluid collecting member which is disposed on the fluid communication member. The additional fluid collecting member preferably has the features of the fluid collecting member as described above. The fluid collecting member and the additional fluid collecting member are preferably disposed in contact with each other on the fluid communication member. This has the advantage that a longer region of the body can be treated. Alternatively, the fluid collecting member and the additional fluid collecting member are preferably disposed apart from each other (i.e. spaced apart from each other) on the fluid communication member. An advantage of these embodiments is that one or more regions of the body can be treated in different ways, by designing the fluid collecting member and the additional fluid collecting member differently. It is preferred that each fluid collection means is separately placed under a negative pressure. It is also possible to perform rinsing treatment and/or suction treatment locally.

The fluid collecting member is preferably designed to conduct a gas and/or a fluid, that more specifically includes particles, from an outer surface of the fluid collecting member to the fluid communication member (or in the reverse direction (for medicines, rinsing, etc.)). The fluid communication member is preferably designed to remove a gas and/or a fluid, that more specifically includes particles, from the fluid collecting member. The fluid collecting member is preferably an open-pored polyurethane sponge. The fluid collecting member preferably has a pore size in a range between 200 μm and 800 μm, and particularly preferably in a range between 400 μm and 600 μm, although other pore sizes are also possible. The fluid communication member is preferably a drainage tube.

Another aspect of the invention relates to a vacuum sponge system comprising a vacuum sponge unit according to the invention and a guide member, in particular a guide wire, and/or a delivery member, in particular a probe unit and/or an endoscope. The embodiments and advantages of the vacuum sponge unit described in the foregoing apply analogous to the vacuum sponge system.

It is preferable that the vacuum sponge system further comprises an overtube for enclosing the vacuum sponge unit, the guide member and/or the delivery member. The overtube has a smaller inner diameter than the outer diameter of the fluid collecting member. The overtube is designed to guide the fluid collecting member in compressed form. The overtube is advantageously used to guide the compressed fluid collecting member along the guide member, in particular along the endoscope, to the intracorporeal region to be treated.

The overtube is preferably slit along its entire longitudinal axis. The overtube is preferably slit between its proximal and distal ends. This has the advantage that the overtube can be placed onto or removed from a guide member and/or delivery member at any time.

The overtube preferably has a first end which is conical in shape and/or a second end which is funnel-shaped. The first end is preferably the distal end and the second end is preferably the proximal end of the overtube. This has the advantage that the distal end can be inserted into the body in a particularly simple manner and can be guided as far as the region to be treated. The advantage of the funnel-shaped end is that the guide member, the delivery member, the vacuum sponge unit and the like can be inserted in a particularly simple manner.

It is preferable that the overtube at least partially comprises an elastically deformable material. The overtube is preferably made of plastic. It is also preferable that the vacuum sponge system also has a positioning sleeve and a guide sleeve, wherein the guide sleeve is designed to be displaceable in relation to the positioning sleeve. The positioning sleeve and/or the guide sleeve preferably consist at least partially of an elastically deformable material, in particular plastic. The overtube, positioning sleeve and/or guide sleeve advantageously allow the vacuum sponge unit to be inserted and positioned in a particularly simple and safe manner.

It is also preferred that the vacuum sponge system further comprises a vacuum pump, in particular an electric vacuum pump, which is connected in fluidic communication to the fluid communication member and is configured to apply a negative pressure of up to 200 mm Hg, preferably 125 mm Hg, to the fluid collecting member. The vacuum pump is preferably designed to be transportable, so that the patient being treated with the vacuum sponge unit according to the invention is mobile.

The guide member is preferably long in relation to its diameter and thin in relation to its length. It is particularly preferred that the guide member is a guide wire, an endoscope and/or a probe unit. The guide member is preferably slit longitudinally. The delivery member is long in relation to its diameter and thin in relation to its length. The guide member and/or the delivery member are preferably embodied like a wire or string. More specifically, the delivery member is preferably a probe unit, a feeding unit, a suction unit, a drainage unit, a rinsing unit, an additional fluid communication member, and/or a working unit, in particular a gripping or cutting unit. The guide member is preferably designed to guide the fluid collecting member to the region to be treated and to position it there. The delivery member is preferably designed for the purposes of supplying, examining, monitoring, processing, etc. the region surrounding the positioned fluid collecting member. The delivery member is also used preferably as a guide member for guiding and positioning the fluid collecting member. This has the advantage that a separate guide member is not necessary in order to position the fluid collecting member, so the vacuum sponge unit can be particularly compact in design and can be inserted in a simple manner into the body. The delivery member preferably includes the guide member. In this way also, the vacuum sponge unit can be given a particularly compact design.

The invention relates, in another aspect, to a method for introducing a vacuum sponge system according to the invention into a human or animal body, said method comprising the steps of disposing the guide member, in particular the guide wire, in the human or animal body, disposing the guide member in the channel of the vacuum sponge unit, and inserting the vacuum sponge unit along the guide member into the human or animal body. The step of disposing the guide member in the channel is preferably performed before, after or simultaneously with the step of disposing the guide member in the body.

Another aspect of the invention relates to a method for manufacturing a vacuum sponge unit according to the invention, said method comprising the steps of disposing a fluid communication member, in particular a drainage tube, at least partially in a fluid collecting member, in particular a sponge unit, connecting the fluid communication member in fluidic communication to the fluid collecting member, forming a channel in the fluid collecting member to guide a guide member, in particular a guide wire, and/or a delivery member, in particular a probe unit and/or an endoscope, through the fluid collecting member. According to the invention, these steps may also be carried out in an order that deviates from the one above.

Another aspect of the invention relates to the use of a fluid collecting material to produce a vacuum sponge unit according to the invention for surgical, endoscopic, gastroenterological or therapeutic treatment of a human or animal body.

Yet another aspect of the invention relates to the use of a vacuum sponge system according to the invention in a human or animal body, such use comprising the steps of disposing the delivery member, in particular the probe unit and/or the endoscope, in the channel of the vacuum sponge unit, inserting or placing the vacuum sponge unit into the human or animal body, and activating the delivery member. The step of disposing the delivery member in the body is preferably performed before, after or simultaneously with the step of inserting or placing the vacuum sponge unit into the body.

Another aspect of the invention relates to using the inventive vacuum sponge unit as a suction attachment.

Embodiments exhibiting combinations of the features described in the foregoing are particularly preferred.

BRIEF DESCRIPTION OF THE DRAWINGS

Preferred embodiments of the invention shall now be described with reference to Figures, in which.

DETAILED DESCRIPTION

Figure 1:
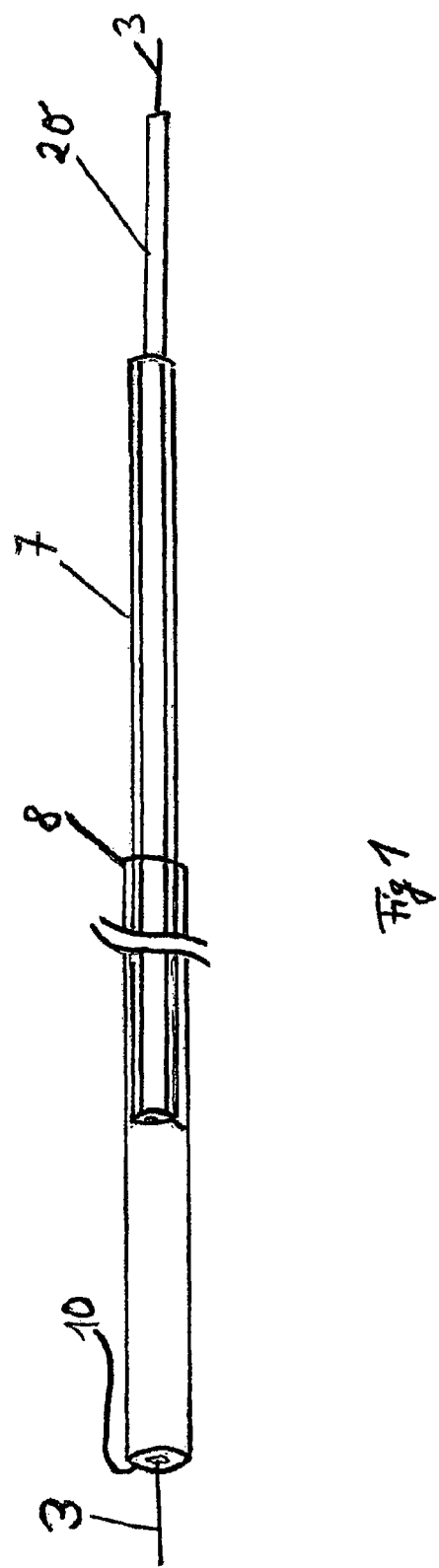
FIGS. 1-7 show an insertion system.

An embodiment according to the invention is shown in FIGS. 1-7. FIG. 1 is a view showing the arrangement of the complete insertion system. The compressed sponge 10, which is connected to drainage line 20, is received at the distal end of guide sleeve 8. A positioning sleeve 7 is likewise inserted into the guide sleeve via drainage line 20 and can be moved in relation to both the guide sleeve and the drainage line.

Guide wire 3 is located inside the drainage line. Said guide wire is initially placed endoscopically over a defect, and the entire insertion system can then be advanced over the wire into position. The sponge has an X-ray-proof marker, so that positioning can be carried out and monitored under X-ray surveillance.

Figure 2:
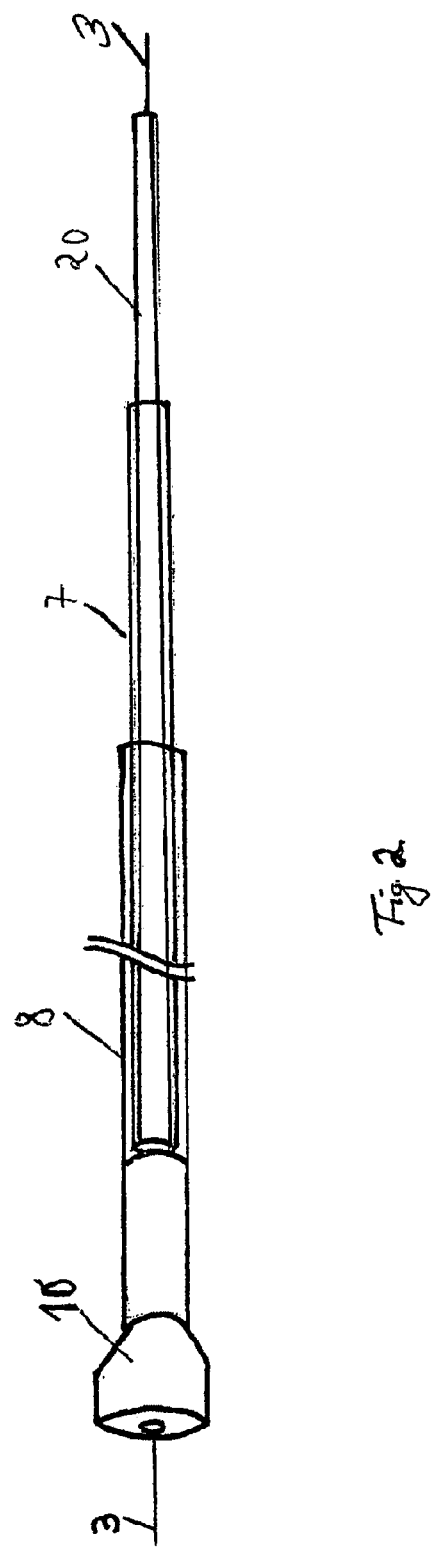
Figure 3:
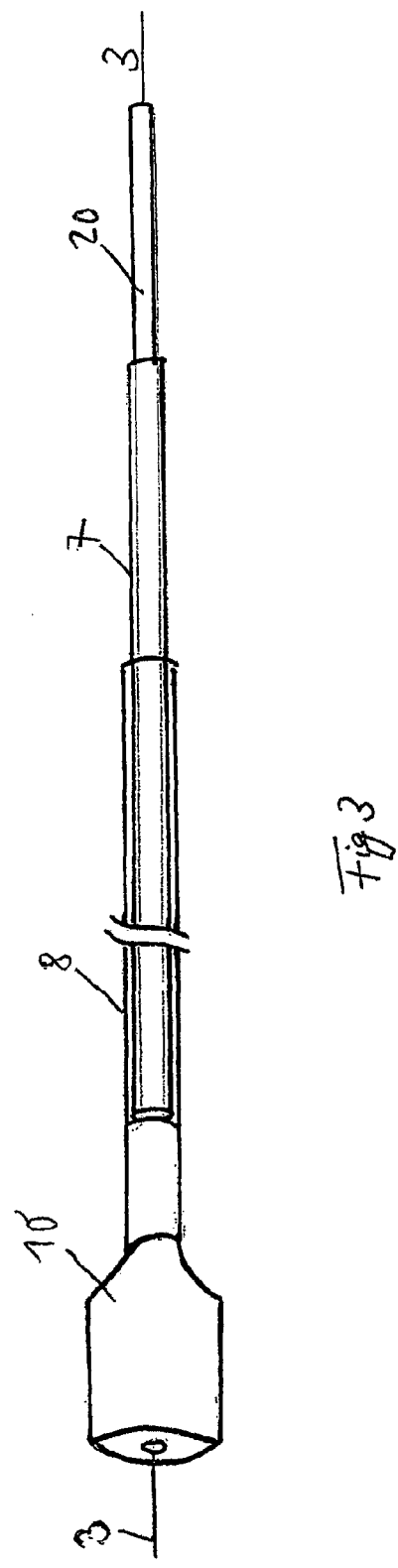
Figure 4:
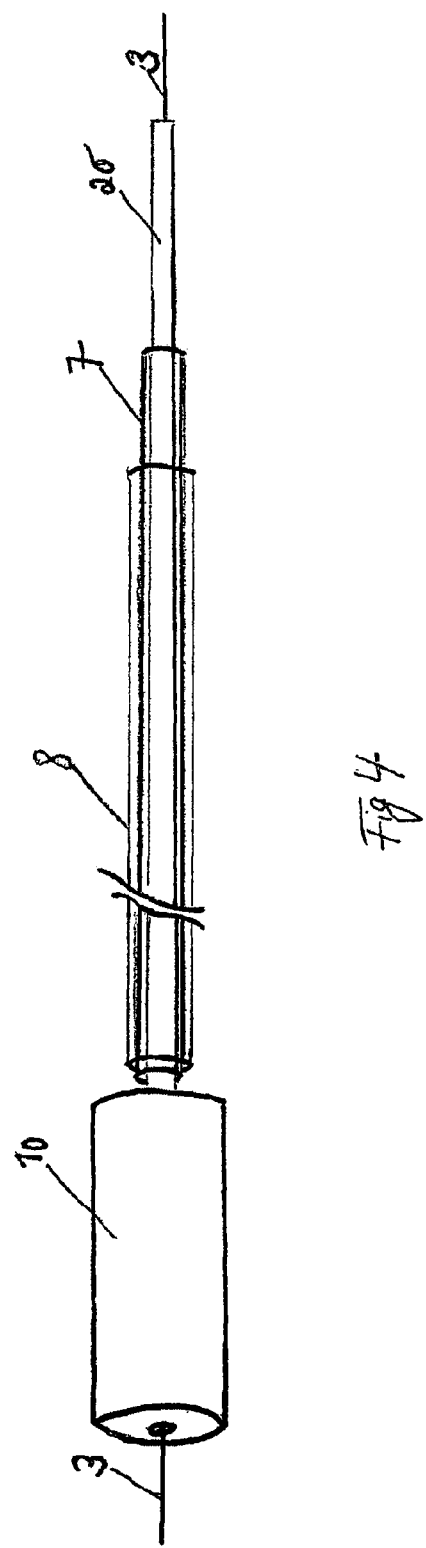
Figure 5:
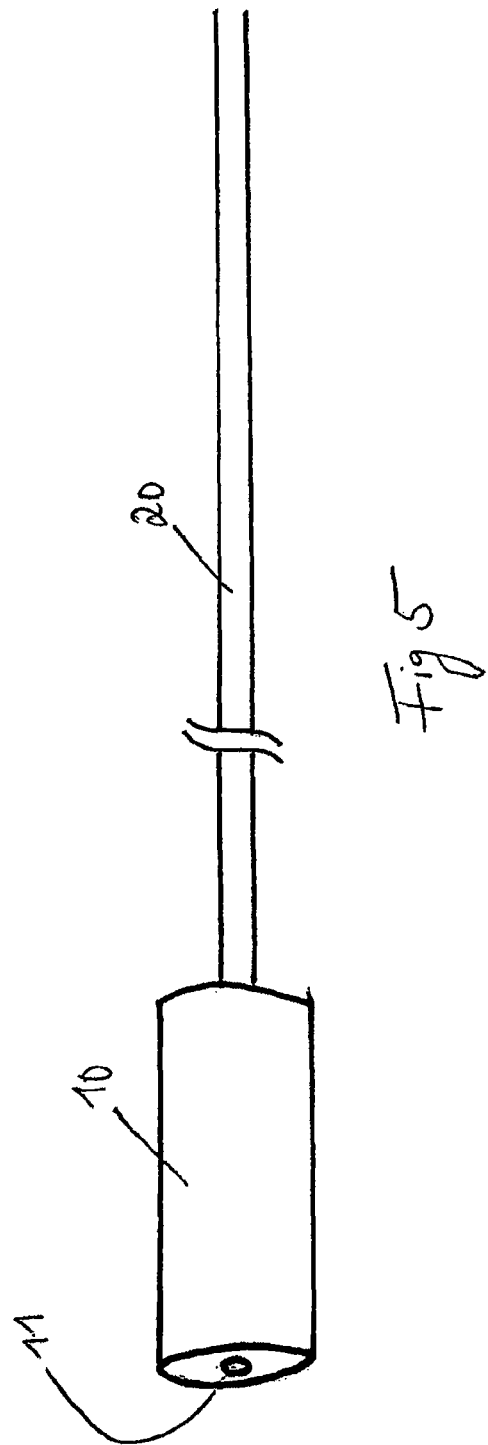

FIG. 2 shows the commencement of sponge 10 being released. Positioning sleeve 7 and guide sleeve 8 are moved towards each other, thus causing the sponge to emerge from the distal end of the guide sleeve. FIG. 3 shows continued release of the sponge. FIG. 4 shows complete release of the sponge. FIG. 5 shows the released sponge after retraction of the guide sleeve, positioning sleeve and guide wire.

Figure 6:
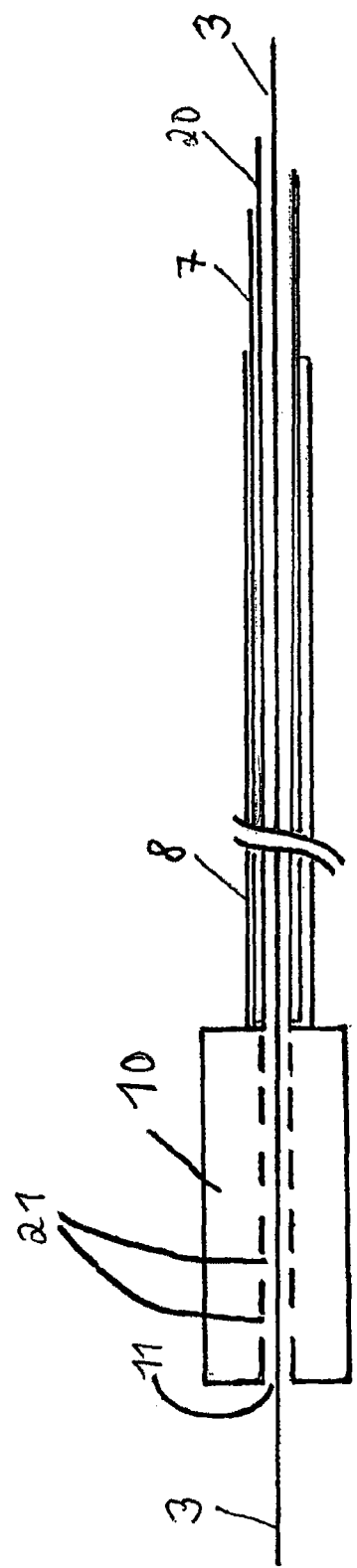
Figure 7:
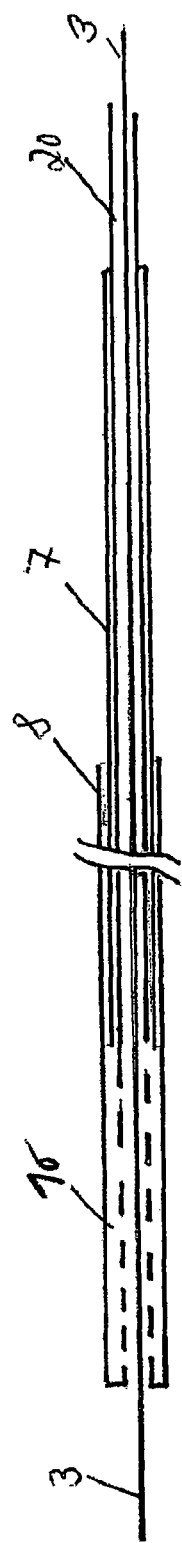

FIG. 6 shows a cross-section through the insertion system when the sponge has been released. Reference sign 21 marks the perforation openings of the drainage line in the sponge. FIG. 7 shows a cross-section through the insertion system, with sponge 10 compressed in the distal end of guide sleeve 8.

Figure 8:
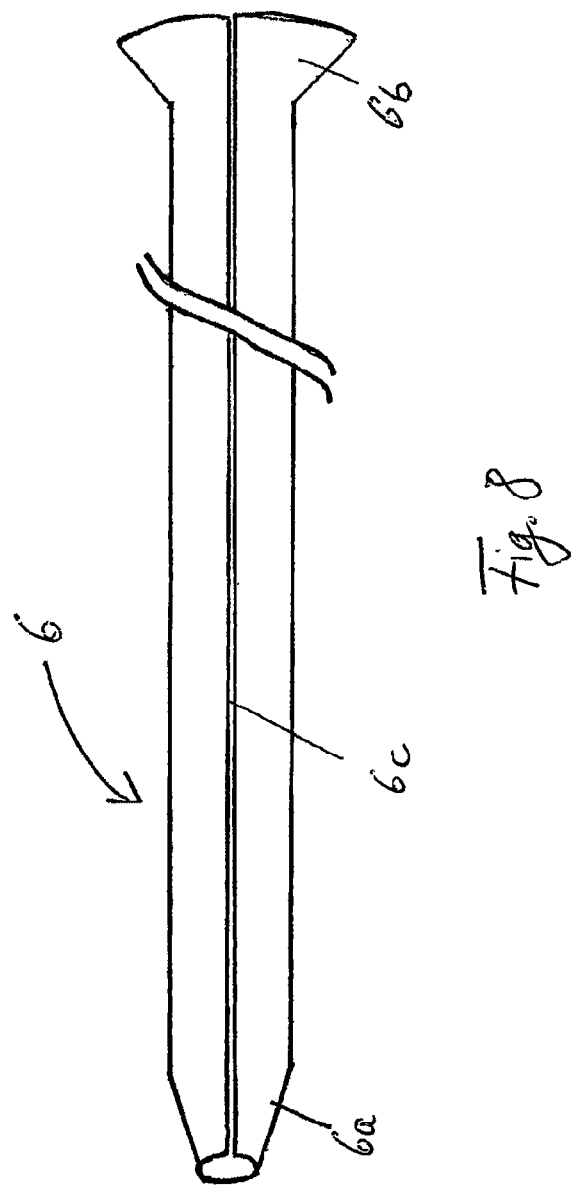
FIGS. 8-15 show an overtube.
Figure 9:
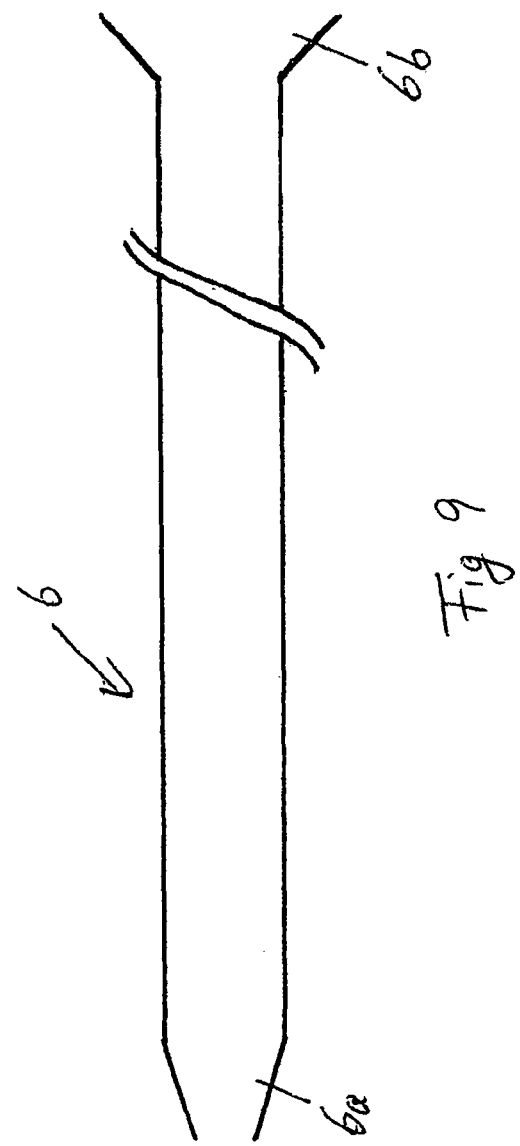

Another embodiment according to the invention is shown in FIGS. 8-15. FIG. 8 is a view showing the design of the overtube. The overtube tapers conically at its distal end 6a, in order to avoid injuries during insertion. A complete slit 6c extends over the entire length of the overtube. The overtube may be funnel-shaped at its proximal end 6b to facilitate insertion of medical instruments. FIG. 9 is a cross-sectional view showing a conical distal end 6a and a funnel-shaped proximal end 6b.

Figure 10:
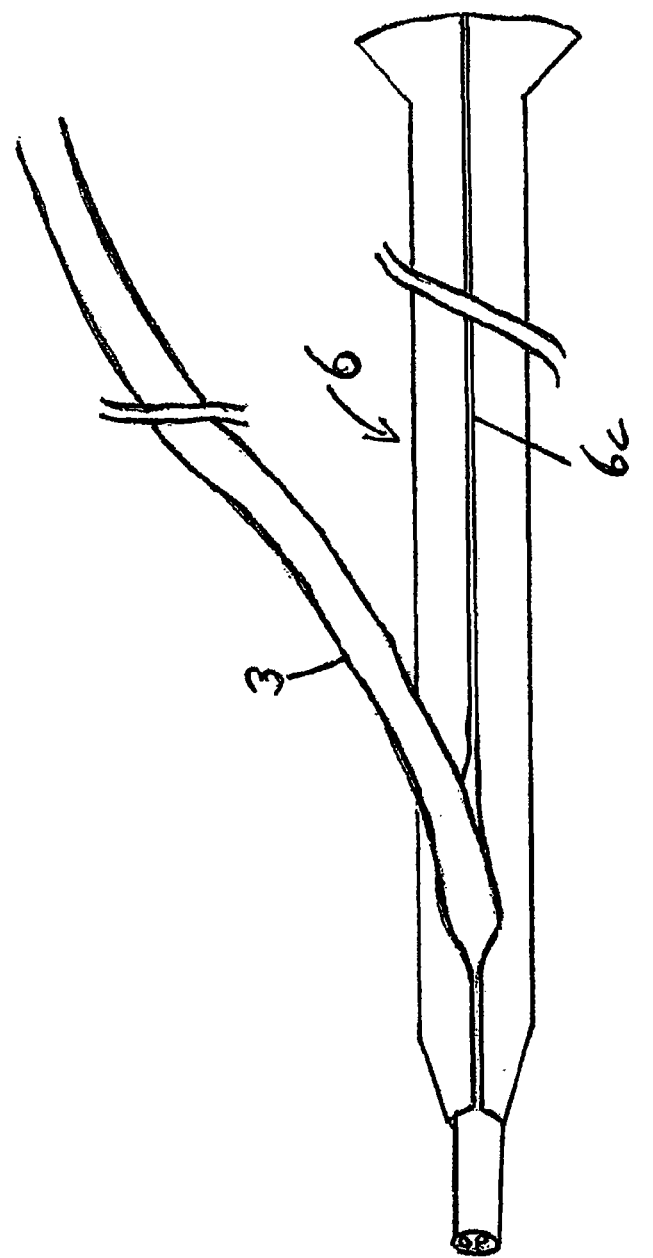
Figure 11:
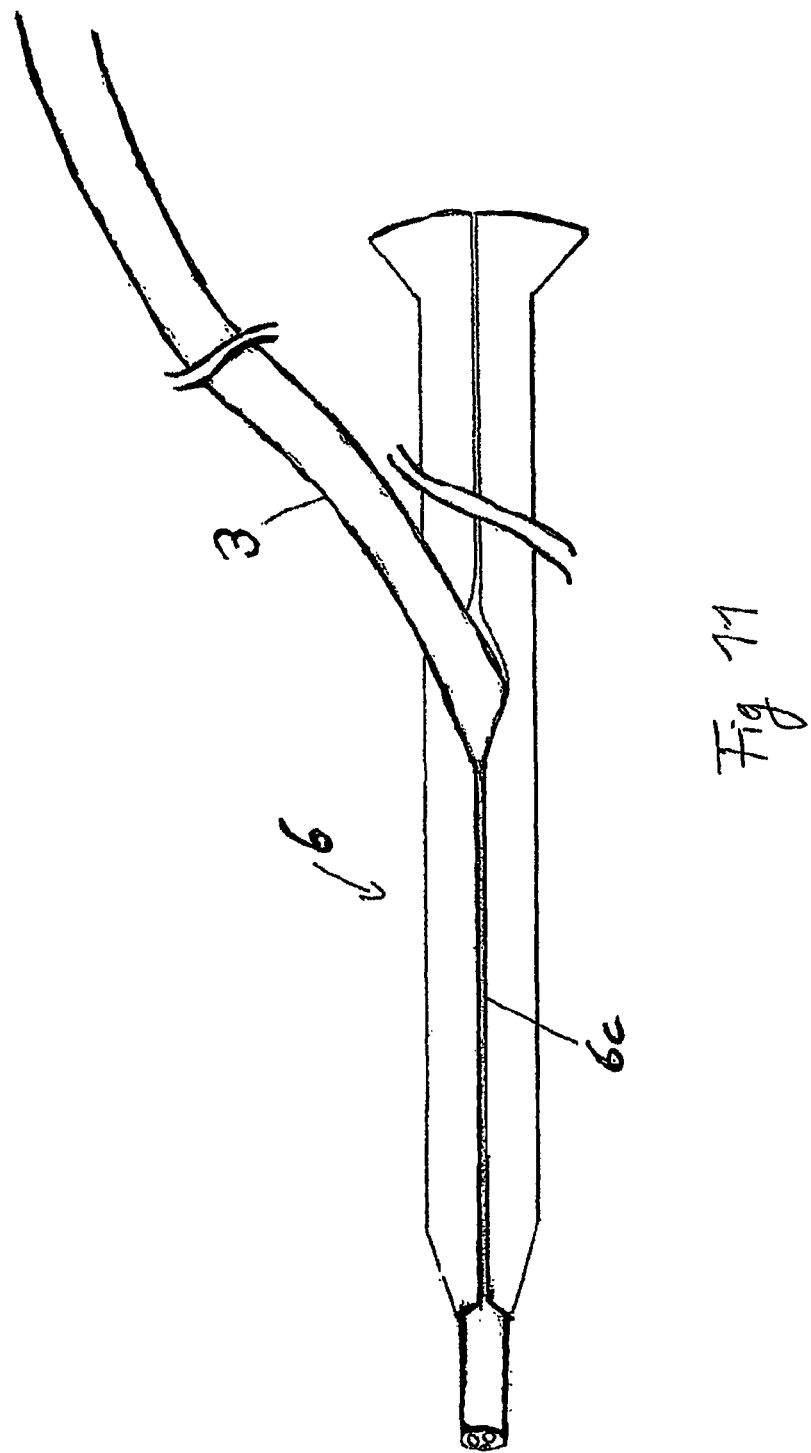
Figure 12:
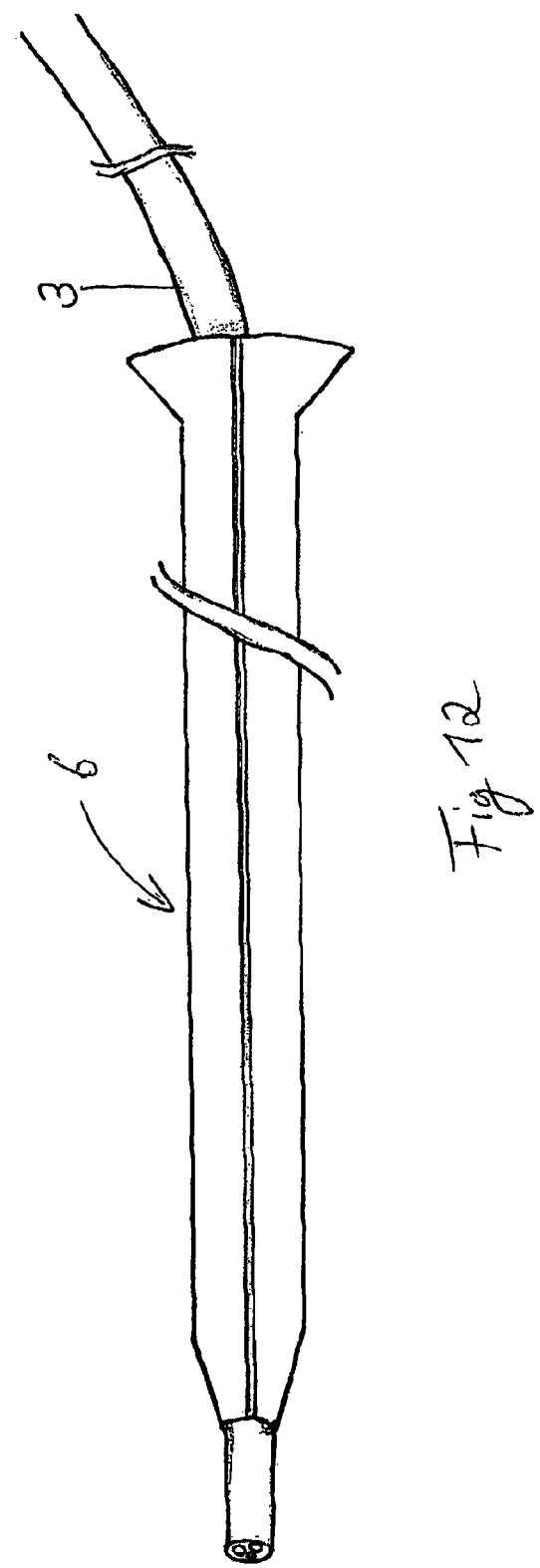

FIG. 10 shows how a flexible endoscope 3 is inserted or retracted via slit 6c at the distal end of the overtube. FIG. 11 shows how a flexible endoscope 3 is inserted into or retracted from the overtube via slit 6c. FIG. 12 shows how a flexible endoscope 3 is fully inserted inside the overtube.

Figure 13:
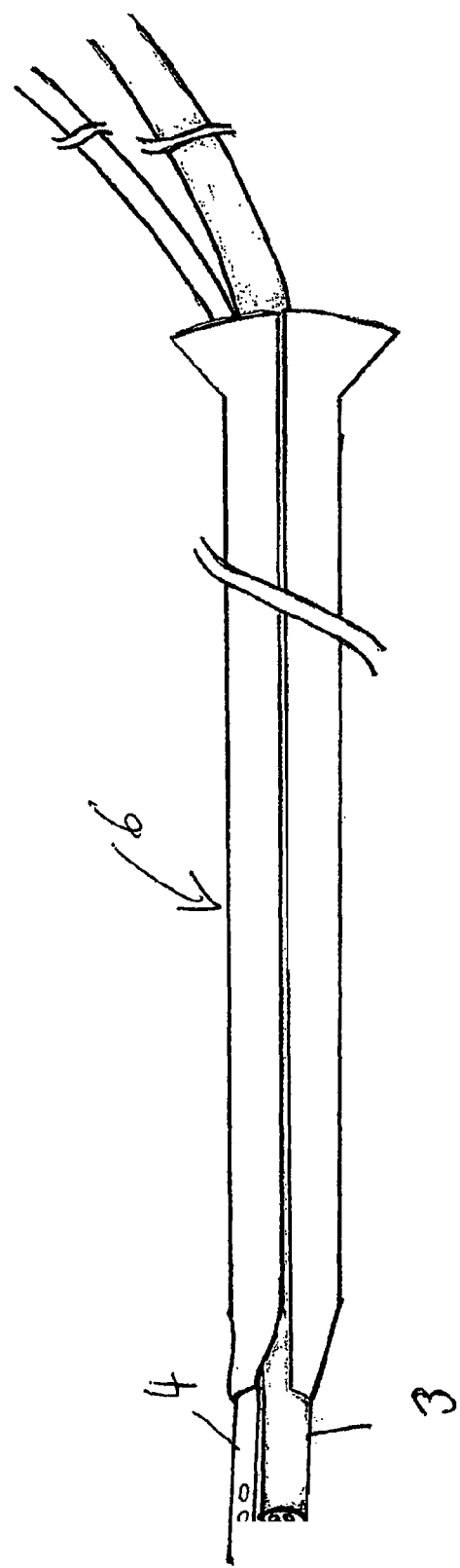
Figure 14:
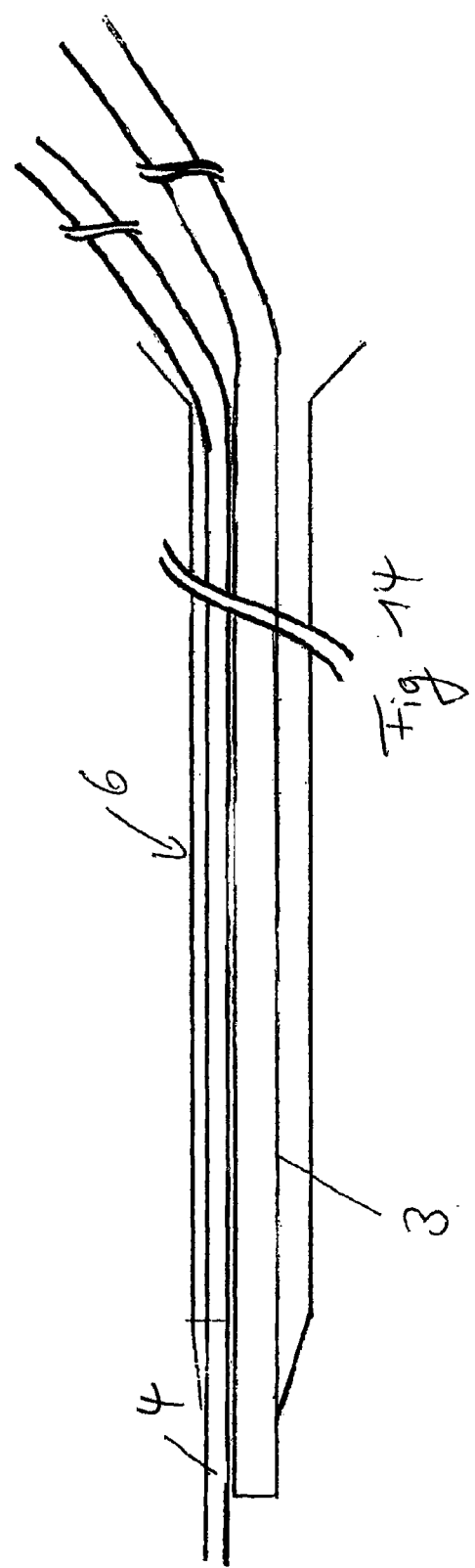
Figure 15:
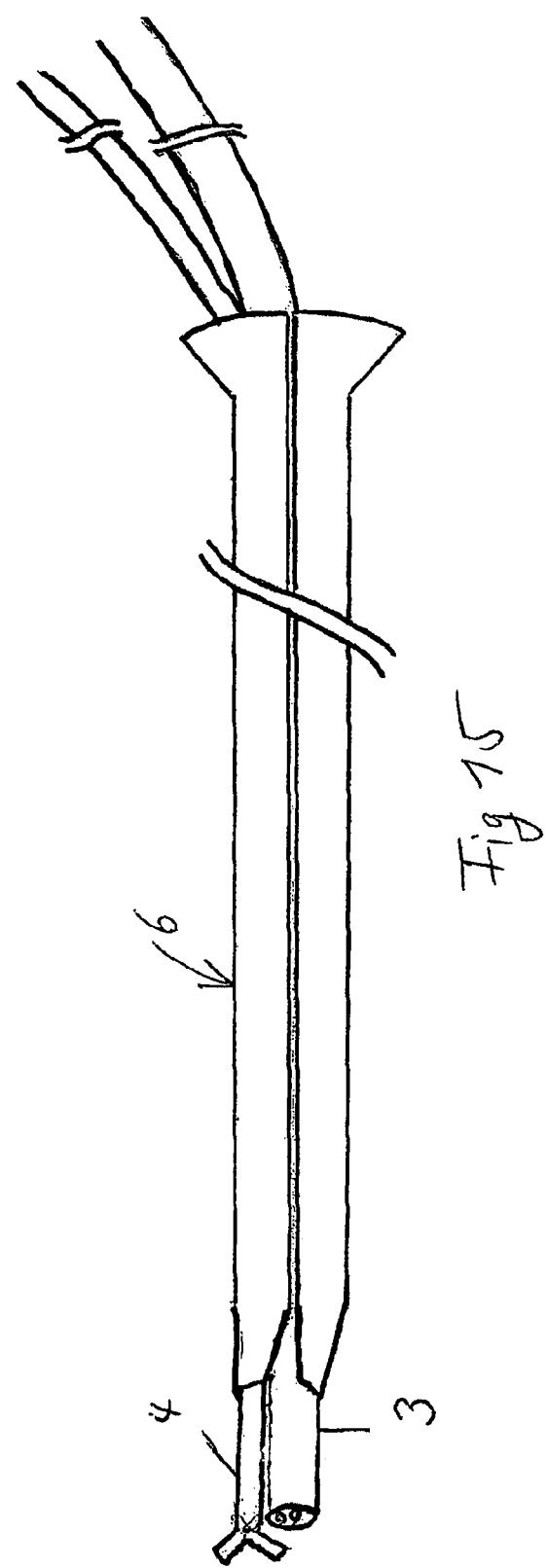

FIG. 13 shows how a drainage line 4 is inserted along with an endoscope 3 in the overtube. FIG. 14 shows a cross-sectional view of an overtube, with an inserted endoscope 3 and a drainage line 4. FIG. 15 shows how a pair of semiflexible endoscopy forceps 4 is inserted as an instrument together with an endoscope.

Figure 16:
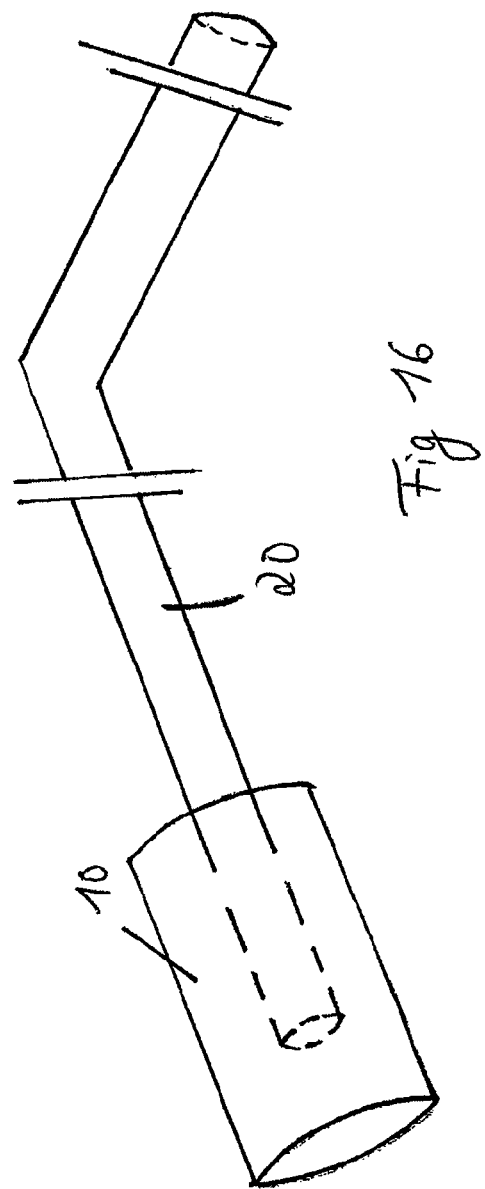
FIGS. 16-21 show a sponge suction attachment.
Figure 17:
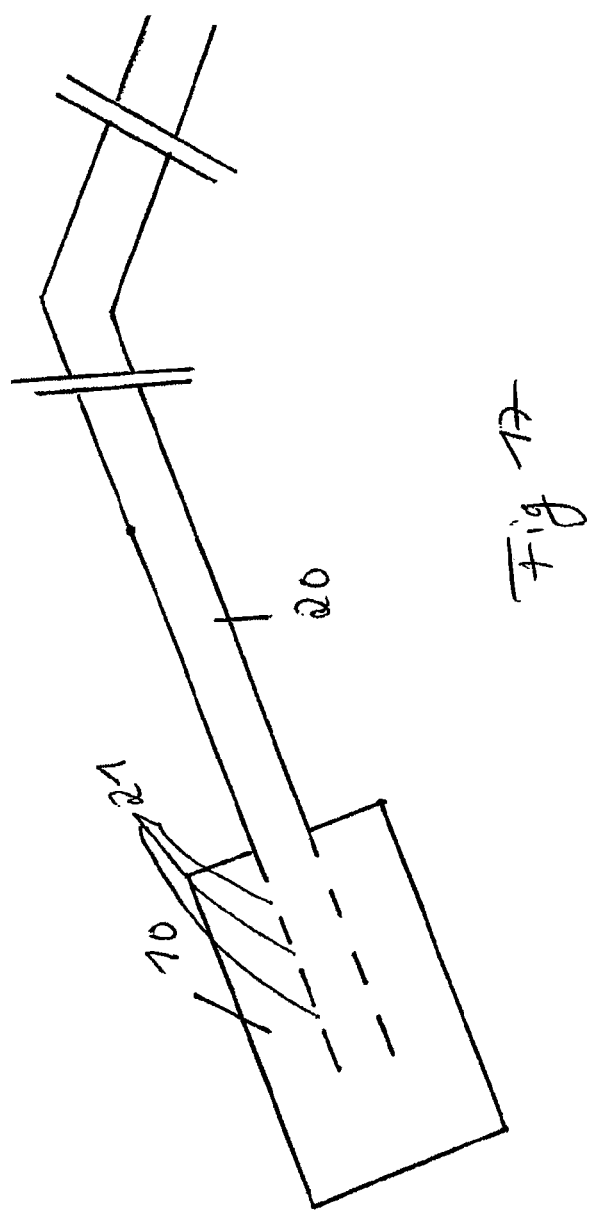

Another embodiment according to the invention is shown in FIGS. 16-21. FIG. 16 shows a view of a kinked drainage tube 20, with a sponge 10 at the distal end of drainage tube 20. FIG. 17 shows the cross-sectional view of FIG. 16.

Figure 18:
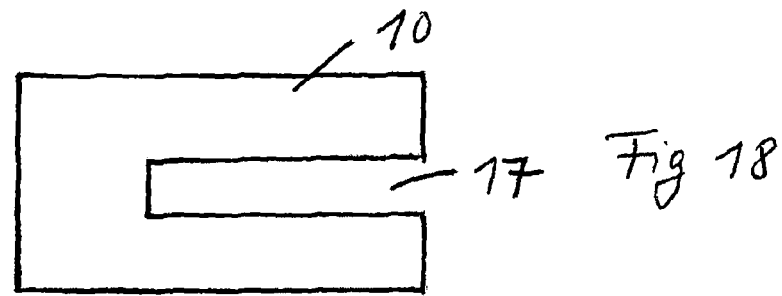
Figure 19:
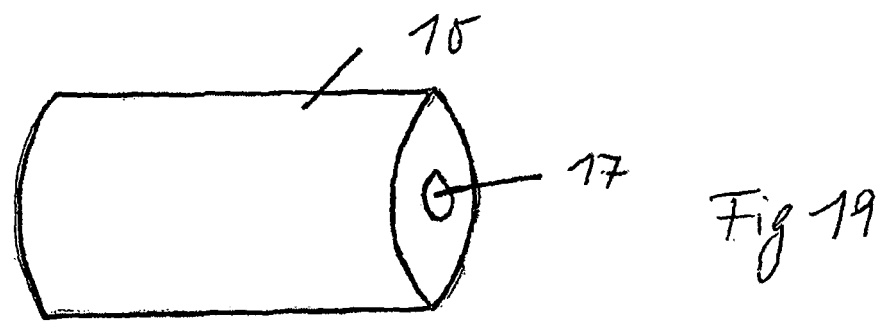
Figure 20:
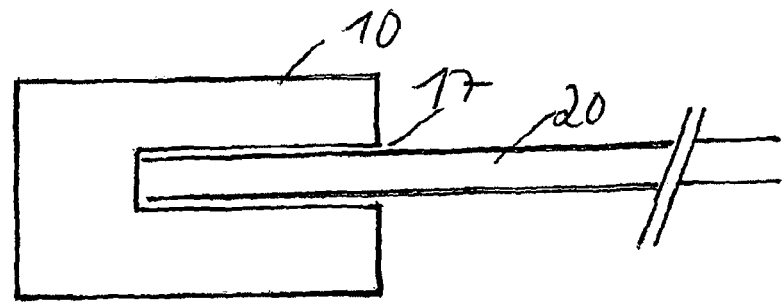

FIG. 18 shows a cross-sectional view of a sponge 10 having a central cavity or recess 17. FIG. 19 shows a three-dimensional view of FIG. 18. FIG. 20 shows a cross-sectional view of a sponge with a central recess 17, into which a drainage tube 20 has been inserted.

Figure 21:
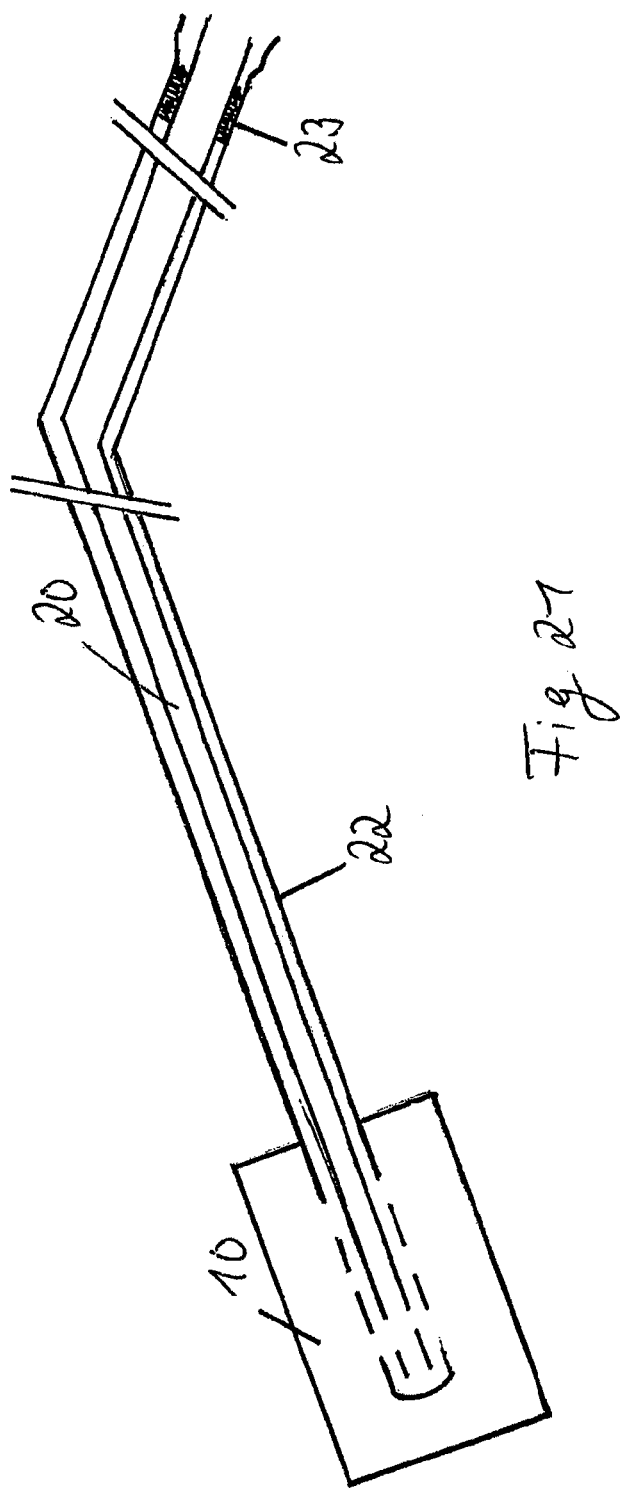

FIG. 21 shows a cross-section of a suction sleeve 22, at the distal end of which a sponge 10 is attached. An additional suction drainage tube 20, which is removable and via which suction can be performed, is inserted into the suction sleeve. Suction sleeve 22 and the suction drainage tube are flushly fitted 23 to each other.

Figure 22:
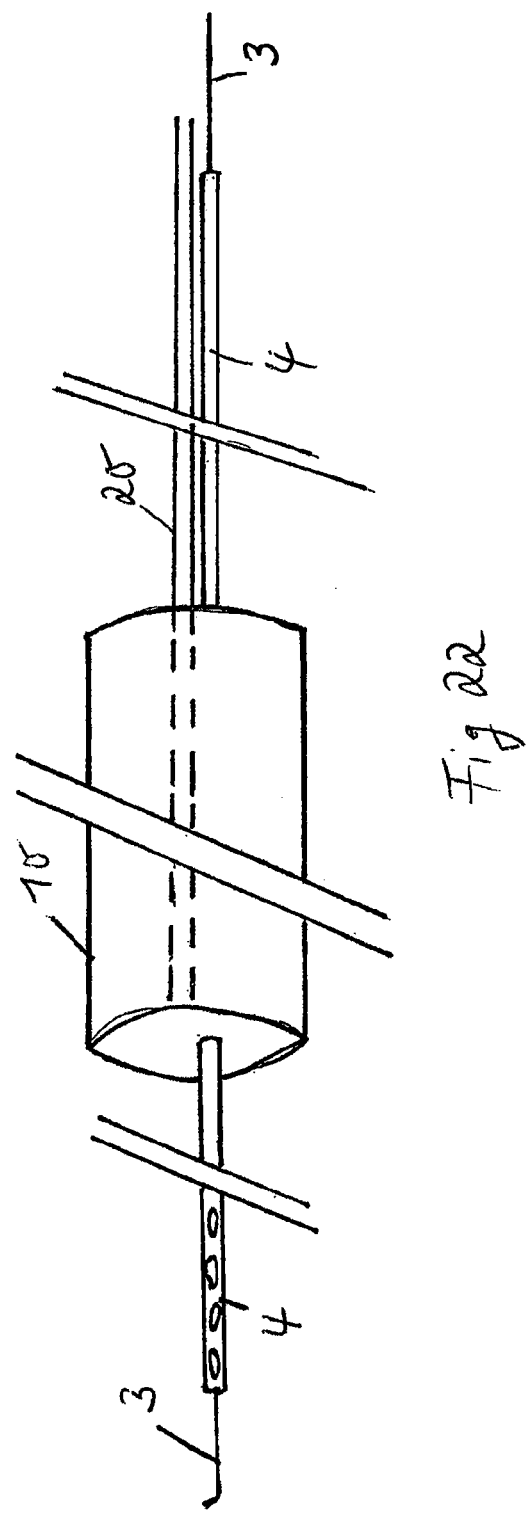
FIGS. 22-26 show a sponge drainage unit.

Another embodiment according to the invention is shown in FIGS. 22-26. FIG. 22 shows a view of the sponge drainage with guide wire 3 disposed in a probe 4 which is guided through sponge 10 and has lateral perforation openings at its distal end and which is disposed in the sponge disposed. The drainage line 20 disposed in sponge 20 is provided at its distal end with perforation openings over the length of the sponge.

Figure 23:
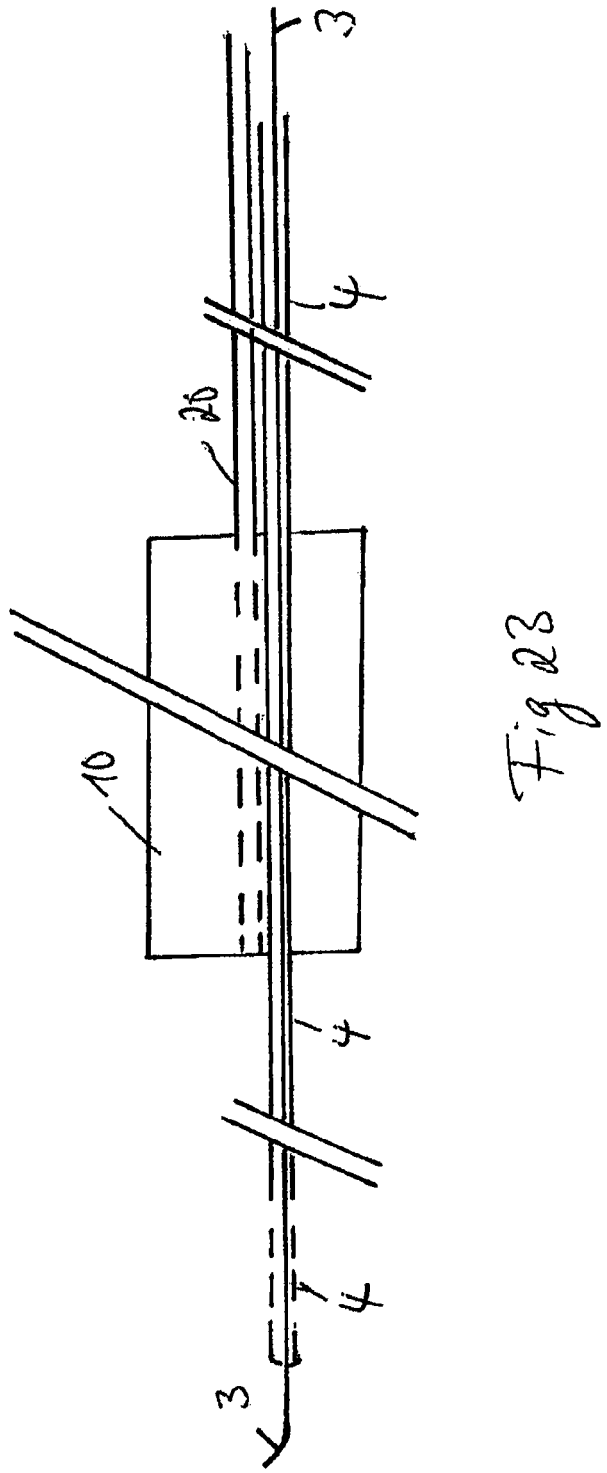
Figure 24:
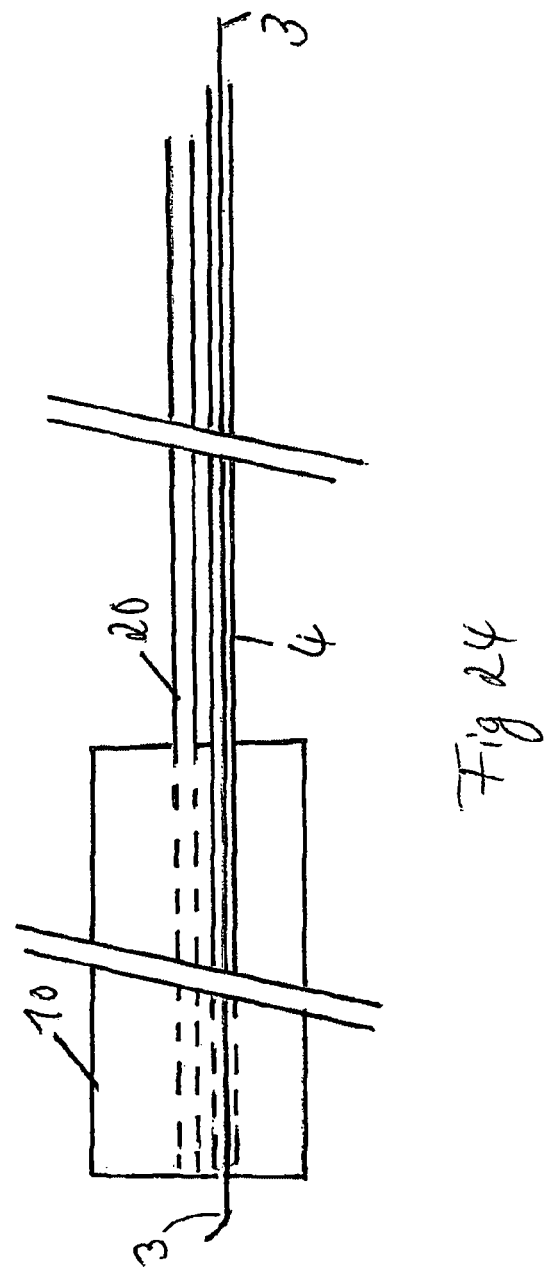

FIG. 23 shows a cross-sectional view of the arrangement in FIG. 22. FIG. 24 shows a cross-sectional view of the arrangement in FIG. 22 in which the probe 4 guided through sponge 10 is designed to be displaceable and has been withdrawn into sponge 10.

Figure 25:
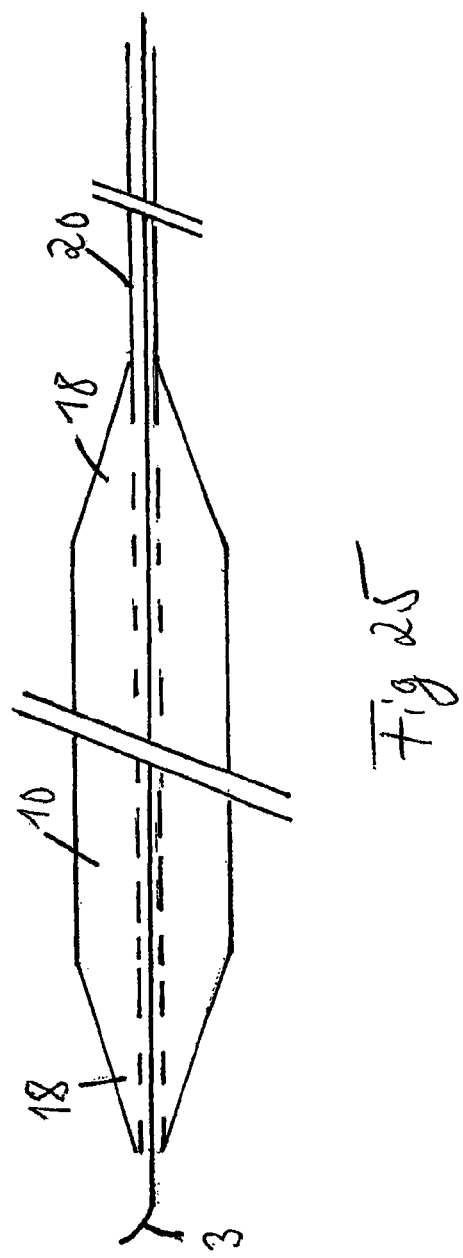
Figure 26:
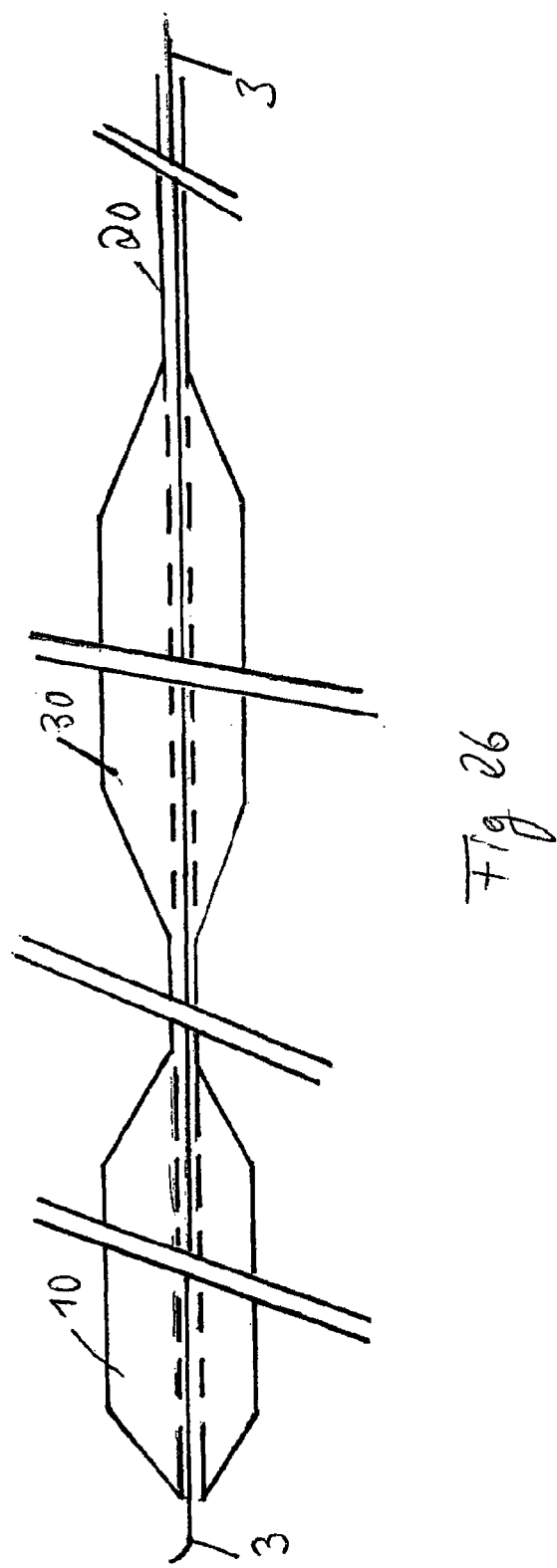

FIG. 25 shows a cross-sectional view of a sponge drainage unit with conically tapering ends 18 to sponge 10, which has been attached to a drainage line 20 having lateral perforation openings over the length of sponge 10. Guide wire 3 is disposed in drainage tube 20. FIG. 26 shows a cross-sectional view of a sponge drainage having two conical sponges 10, 30, a guide wire 3 and a drainage tube 20.

Figure 27:
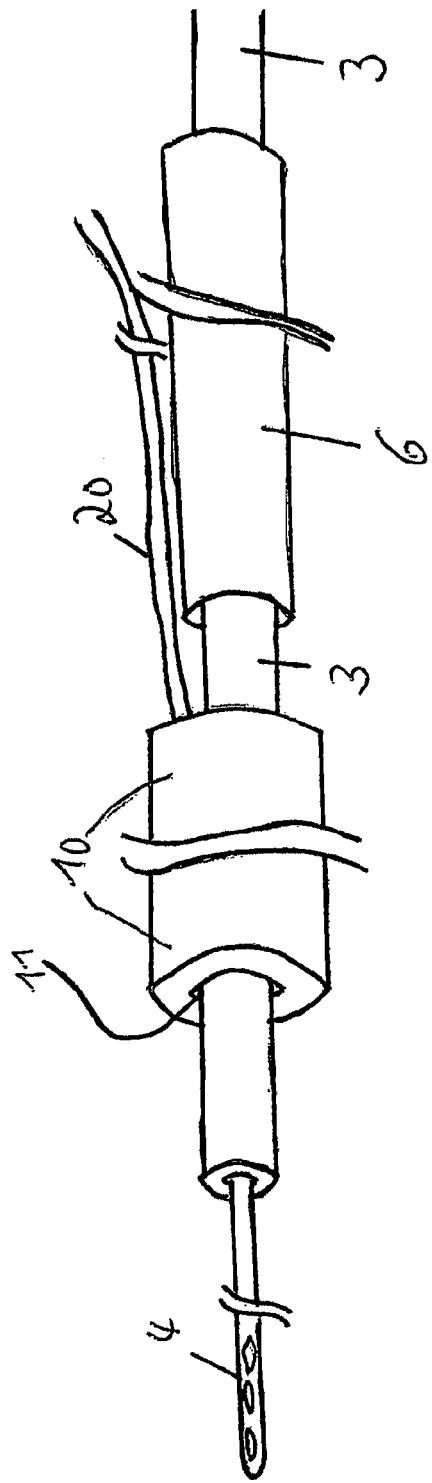
FIGS. 27-32 show a drainage system.

Another embodiment according to the invention is shown in FIGS. 27-32. FIG. 27 is a view showing the arrangement of the complete drainage system (tubular sponge 10 and drainage tube 20) on the distal end of a flexible endoscope 3 guided through an overtube 6. A feeding tube 4 has already been advanced through the working channel of the endoscope.

Figure 28:
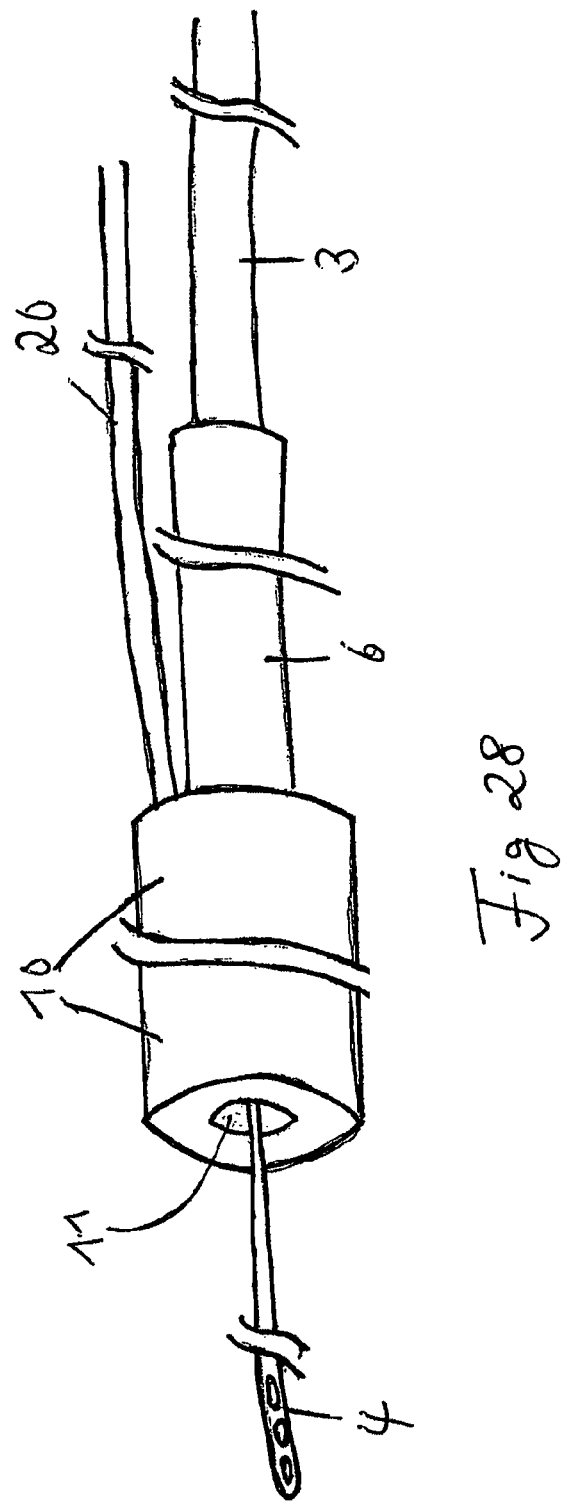
Figure 29:
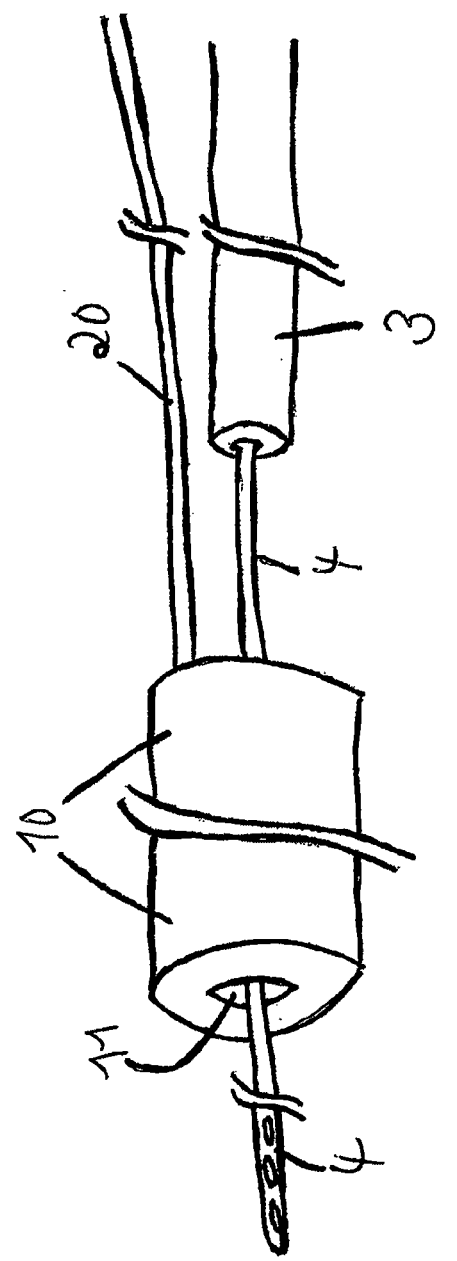

FIG. 28 shows how release of sponge 10 is handled. The overtube 6 is guided in a distal direction on endoscope 3. The sponge slips over the distal end of the endoscope. FIG. 29 shows how sponge 10 is finally released. At this moment, a negative pressure can be applied via drainage tube 20. Due to the negative pressure being applied to an intestinal lumen or in a cavity, the sponge adheres to tissue and the feeding tube 4 is simultaneously fixed inside the sponge.

Figure 30:
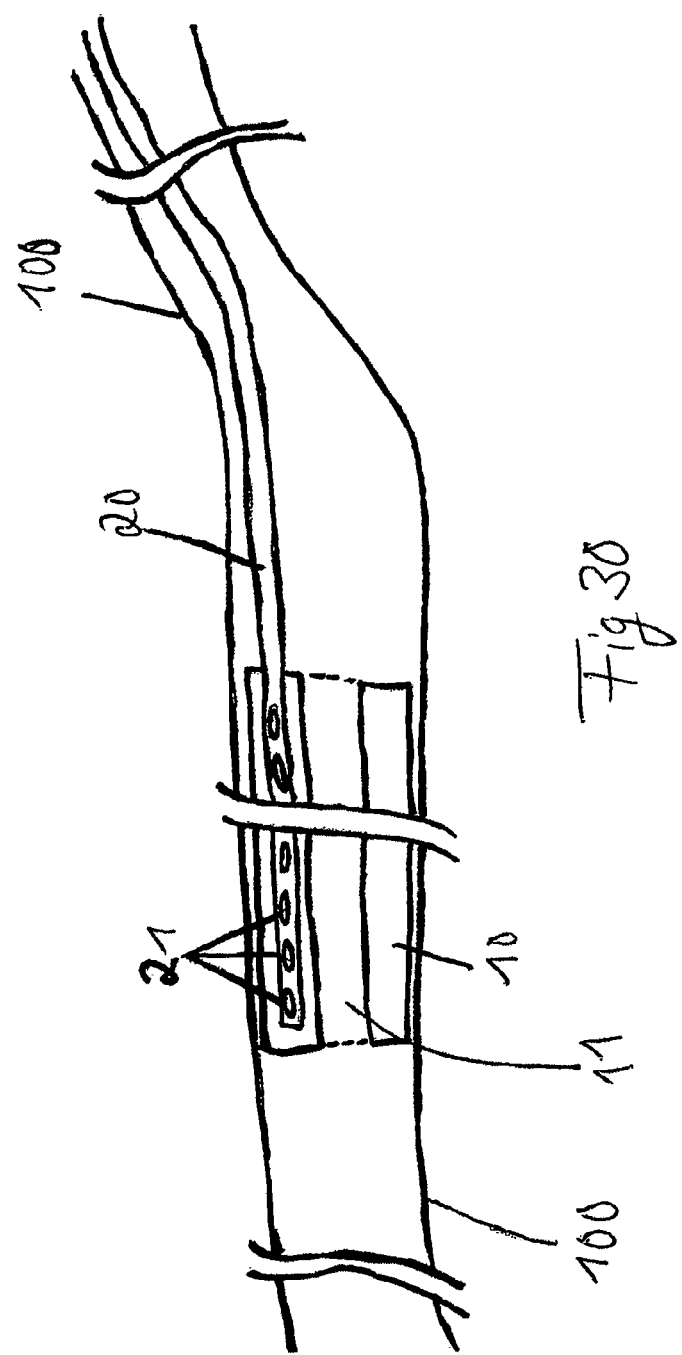
Figure 31:
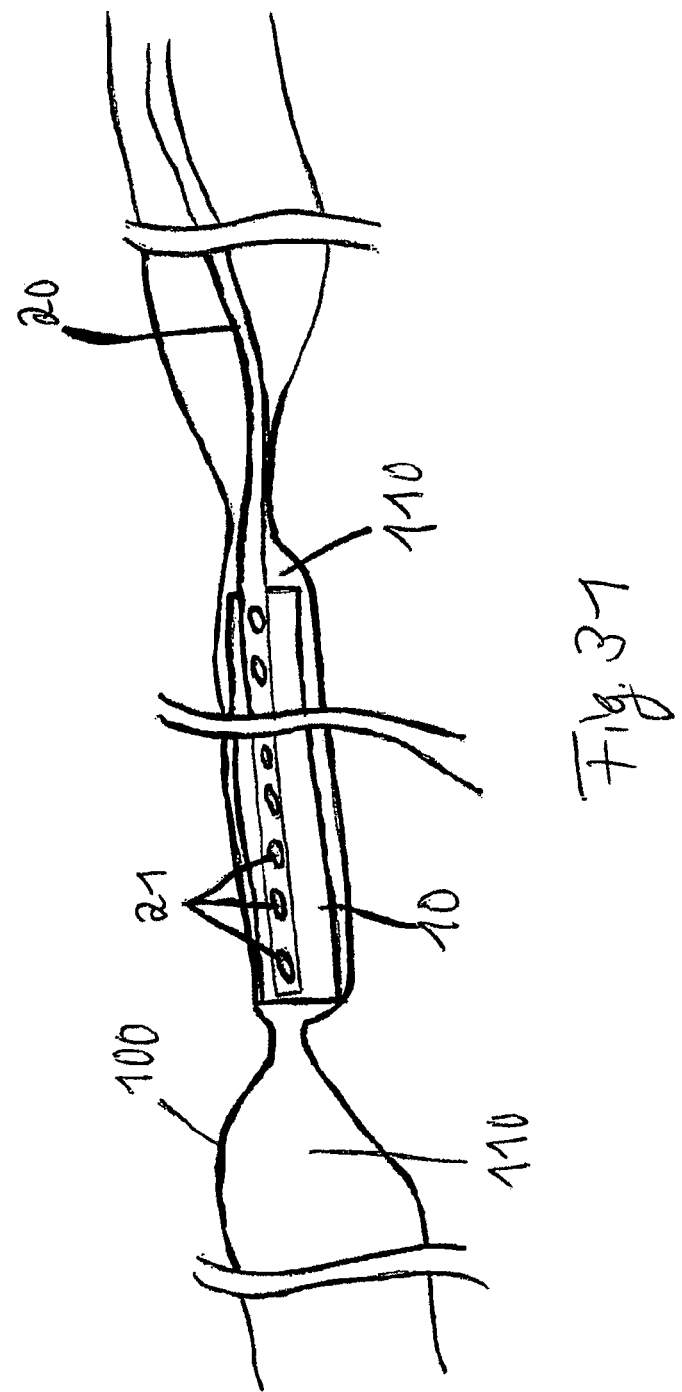

FIG. 30 shows a cross-sectional view of a sponge 10 placed in an intestine 100, with drainage tube 20. There are perforation openings 21 at the distal end of drainage tube 20, inside sponge 10. FIG. 31 shows a sponge 10 which is placed in an intestine 100 and which has collapsed under a vacuum. This also causes the intestinal lumen 110 to collapse onto sponge 10 and results in artificial closure of intestinal lumen 110. Perforation openings 21 are provided at the distal end of drainage tube 20.

Figure 32:
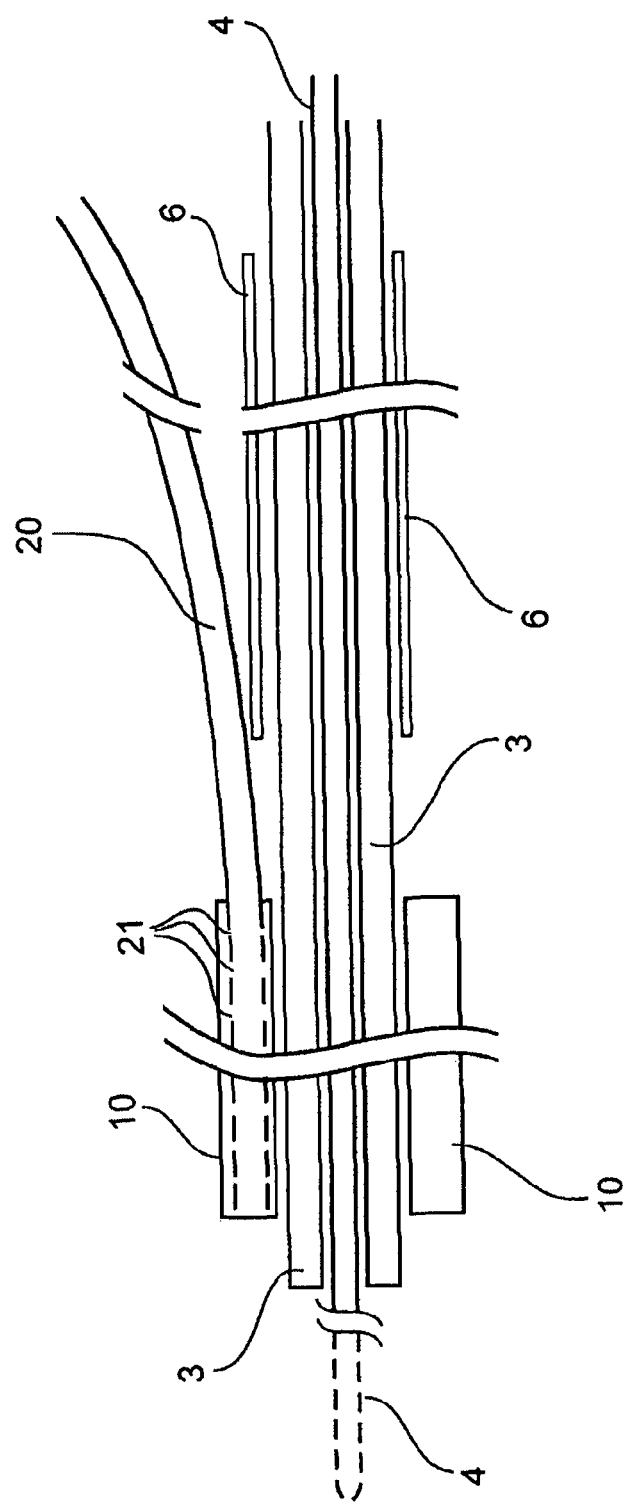

FIG. 32 shows a cross-sectional view of the entire drainage system (tubular sponge 10, drainage tube 20 with perforation openings 21 at its distal end) mounted on the distal end of an endoscope 3. Endoscope 3 lies inside an overtube 6. There is a feeding tube 4 in the working channel of endoscope 3.

Figure 33:
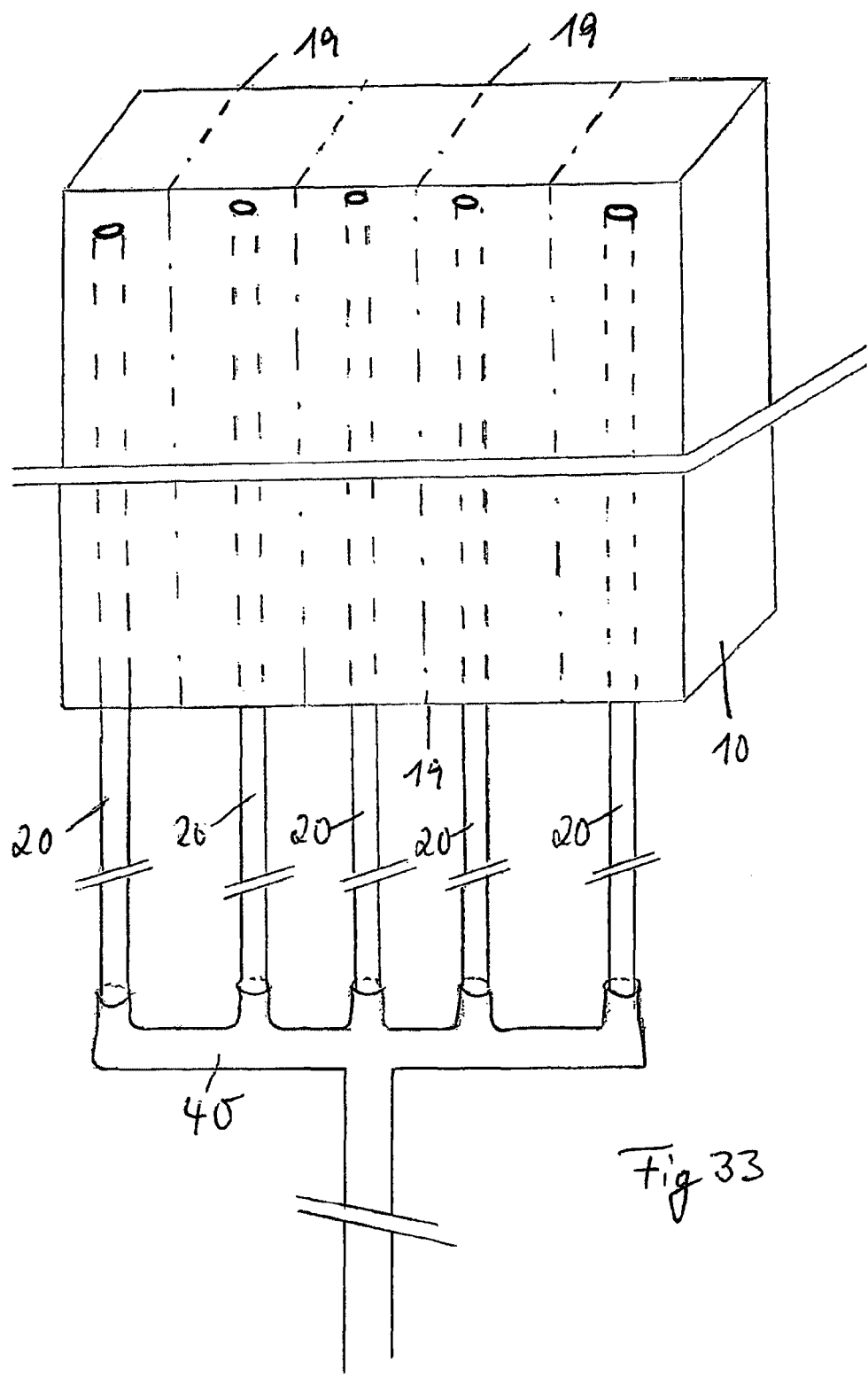
FIGS. 33-37 show another drainage system.
Figure 34:
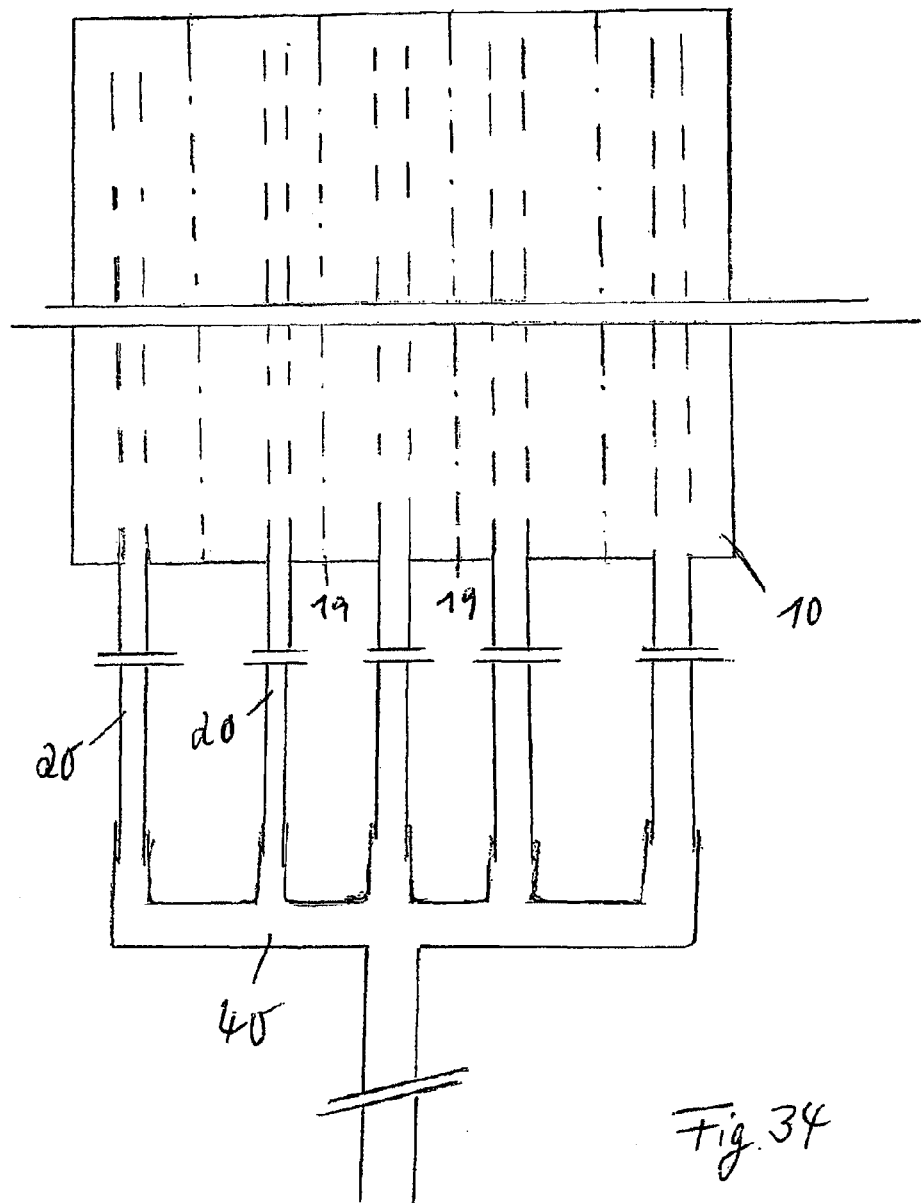

Another embodiment in accordance with the invention is shown in FIGS. 33-37. FIG. 33 shows a view of a sponge 10 into which a plurality of drainage tubes 20 perforated at their distal end have been inserted. Drainage tubes 20 are connected to each other via a connector member 40. The sponge is perforated between the drainage tubes (perforation line 19). FIG. 34 shows a cross-sectional view of FIG. 33.

Figure 35:
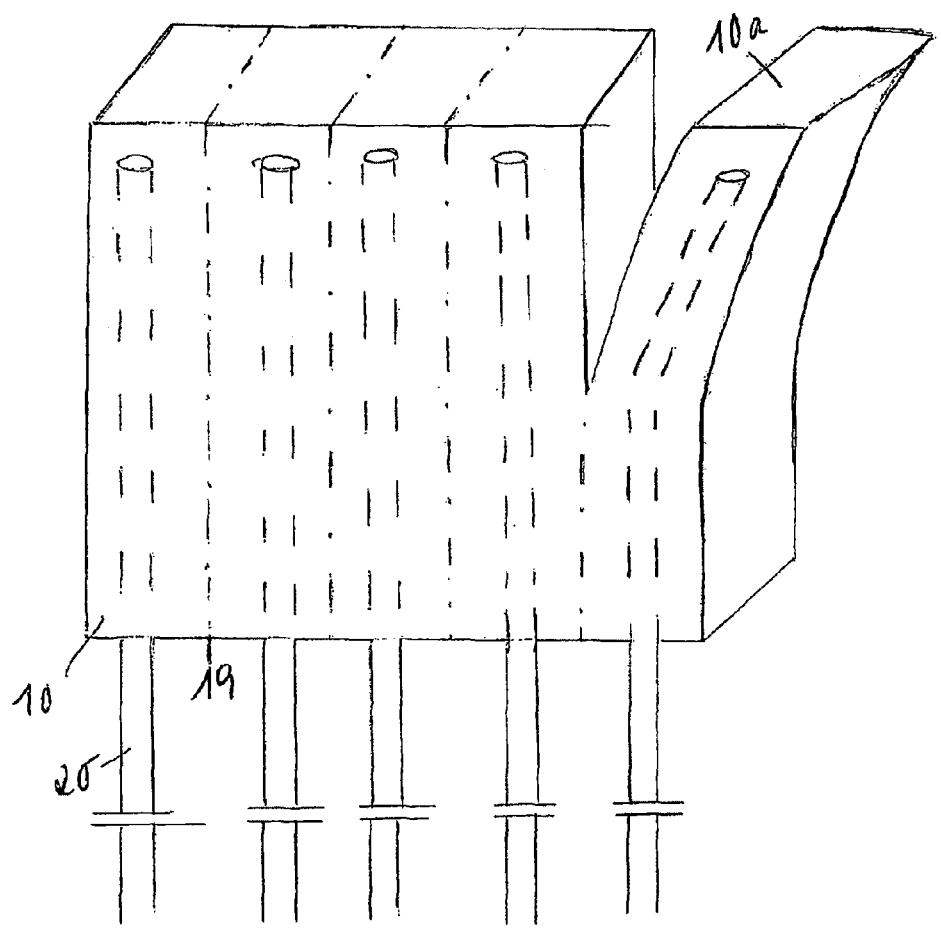
Figure 36:
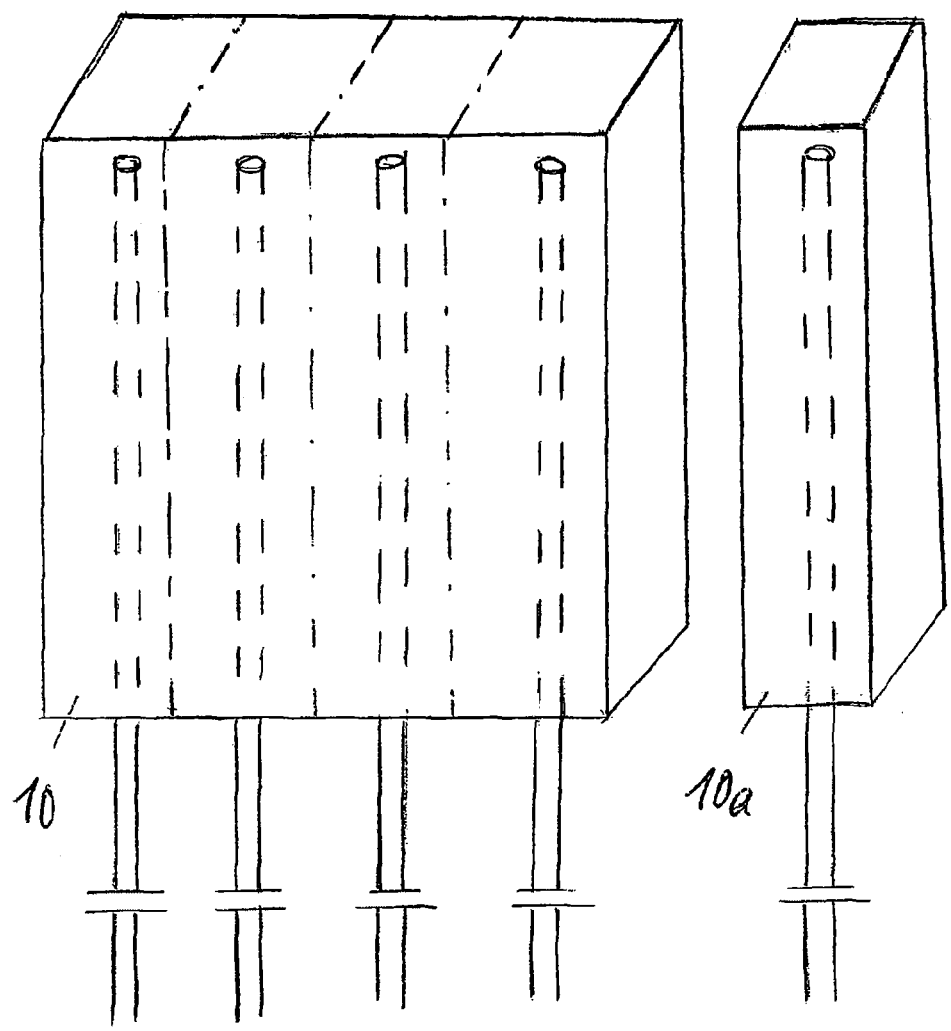

FIG. 35 shows the separation of a subunit 10a from sponge 10. FIG. 36 shows the complete separation of a subunit 10a from sponge 10.

Figure 37:
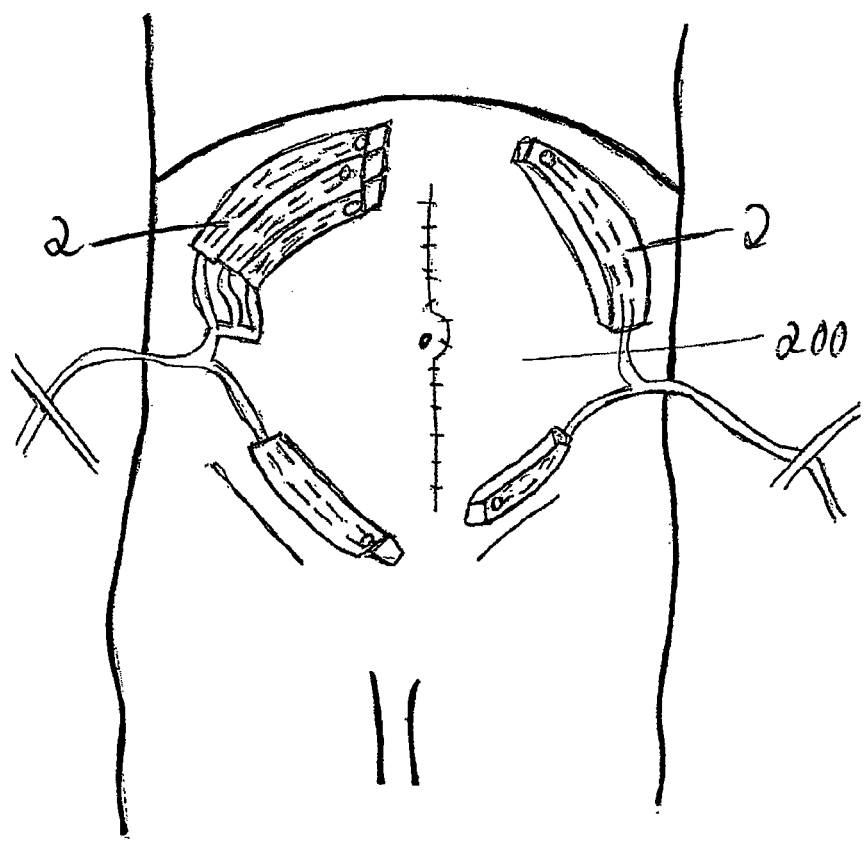

FIG. 37 shows a schematic view of vacuum sponge drainage units 2 of different sizes arranged in the abdominal cavity 200.

In the Figures, the inventive channel in the fluid collecting member is marked with the reference sign 11.

The features described with reference to FIGS. 8-15 apply analogously to the slit fluid collecting member.

Although FIGS. 16-21 illustrate only a recess 17, a channel 11 according to the invention may be provided in the advantageous manner described in the foregoing. The fluid collecting member is advantageously embodied in cap-like form, and the fluid communication member does not extend along the entire length of the fluid collecting member.

FIGS. 33-37 illustrate a plurality of fluid communication members. A channel 11 according to the invention may additionally be provided. Each of subunits 10a is preferably embodied as described with reference to FIGS. 16-21. In another embodiment, subunits 10a are a vacuum sponge unit according to the invention.

The invention claimed is:

1. A vacuum sponge unit for use in human or animal bodies, comprising:
  a fluid collecting member comprising a sponge unit having a plurality of subunits pre-perforated at their boundaries, wherein the subunits are separable from one another; and
  a fluid communication member comprising a plurality of drainage tubes, wherein each of the drainage tubes is disposed at least partially in one of the subunits, and wherein each subunit has at least one of the drainage tubes at least partially disposed therein; and
  wherein each of the drainage tubes is in fluid communication with one of the subunits such that negative pressure can be applied to all of the subunits after one or more subunits have been separated.

2. The vacuum sponge unit according to claim 1, wherein the fluid collecting member further comprises an X-ray marker designed to be detected during roentgenography.

3. The vacuum sponge unit according to claim 1, wherein at least one drainage tube extends along the entire length of at least one subunit.

4. The vacuum sponge unit according to claim 1, wherein the fluid communication member is configured to be connected in fluid communication with a vacuum pump.

5. The vacuum sponge unit according to claim 1, wherein at least one drainage tube is fixedly connected to at least one subunit.

6. The vacuum sponge unit according to claim 1, wherein at least one drainage tube has a plurality of openings in the region disposed in at least one subunit.

* * * * *